United States Patent
Dorundo et al.

[11] Patent Number: 5,926,266
[45] Date of Patent: Jul. 20, 1999

[54] OPTICAL APPARATUS FOR RAPID DEFECT ANALYSIS

[75] Inventors: Alan D. Dorundo, Boca Raton; Michael Gerard Lisanke, Boynton Beach; Huizong Lu, Coconut Creek; Richard J. McCormick, Light House Point; Lanphuong Thi Pena, Fort Lauderdale; Eric V. Schnetzer, Boynton Beach; Ali Reza Taheri, Boca Raton, all of Fla.

[73] Assignee: International Business Machines Corporation, Armonk, N.Y.

[21] Appl. No.: 08/710,805

[22] Filed: Sep. 23, 1996

Related U.S. Application Data

[51] Int. Cl.[6] ........................................... G01J 21/00
[52] U.S. Cl. ..................... 356/237.2; 356/338; 356/337; 356/445
[58] Field of Search .................... 356/237, 338, 356/337, 445

[56] References Cited

U.S. PATENT DOCUMENTS

| | | | |
|---|---|---|---|
| 4,298,283 | 11/1981 | Makosch et al. | 356/351 |
| 4,320,973 | 3/1982 | Fortunato et al. | 356/346 |
| 4,534,649 | 8/1985 | Downs | 356/351 |
| 4,844,616 | 7/1989 | Kulkarne et al. | 356/351 |
| 5,062,021 | 10/1991 | Ranjan et al. | 360/135 |
| 5,108,781 | 4/1992 | Ranjan et al. | 427/53.1 |
| 5,122,648 | 6/1992 | Cohen et al. | 250/201.3 |
| 5,225,886 | 7/1993 | Koizumi et al. | 356/237 |
| 5,289,260 | 2/1994 | Miyazaki et al. | 356/354 |
| 5,293,211 | 3/1994 | Bernard | 356/124 |
| 5,469,259 | 11/1995 | Golby et al. | 356/351 |

FOREIGN PATENT DOCUMENTS

| | | | |
|---|---|---|---|
| 1392395 | 4/1975 | United Kingdom | G05B 11/01 |

OTHER PUBLICATIONS

T. Bayer and G. Makosch, Photolithgraphic Process Control by Optical Phase Monitoring of Latent Images in Photoresist, *IBM Tech. Disclosure Bulletin*, vol. 34, No. 10A, Mar., 1992, pp. 140–143.

U. Frank–Schmidt and G. Makosch, Interferometric Method of Checking the Overlay Accuracy in Photolithographic Exposure Processs, *IBM Tech. Disclosure Bulletin*, vol. 32, No. 10B, Mar. 1990, pp. 214–217.

G. Makosch, System for Stepless Beam Splitting, *IBM Tech. Disclosure Bulletin*, vol. 30, No. 11, Apr. 1988, pp. 249–250.

H. Korth and F. Schedwie, Analyzing Optical Phase Structures, *IBM Tech. Disclosure Bulletin*, vol. 24, No. 6. Nov., 1981, pp. 3094–3095.

*Primary Examiner*—Frank G. Font
*Assistant Examiner*—Reginald A. Ratliff
*Attorney, Agent, or Firm*—Richard A. Tomlin; Ronald V. Davidge

[57] ABSTRACT

Apparatus for inspecting the surface of a sample includes a wide scanning interferometer, which is used to locate defects, or anomalies in the surface, and a narrow scanning interferometer, which is used to develop profiles of individual defects found by the narrow scanning interferometer. The sample may be driven in rotation about an axis, while the interferometers are independently moved radially to the axis.

24 Claims, 13 Drawing Sheets

OPTICAL APPARATUS FOR RAPID DEFECT ANALYSIS

CROSS REFERENCE TO A RELATED APPLICATION

This application is related to a co-pending U.S. application Ser. No. 08/426,778, filed Apr. 11, 1995, entitled "Apparatus and Method for Acquiring and Analyzing Interferometric Images," by Alan. D. Dorundo, et al., having a common assignee with the present invention, the disclosure of which is hereby incorporated for reference. This application describes a method for acquiring and analyzing interferometric images first to locate surface defects using moving images produced by a scanning motion, and then to analyze the defects found in this way using a static imaging method.

A co-pending U.S. application, Ser. No. 08/710,807 entitled "Optical Differential Profile Measurement and Apparatus," filed on the same day as the present application, and having a common assignee therewith, describes an interferometer configured particularly to determine a difference in height between two spaced-apart test spots on a test surface.

A co-pending U.S. application, Ser. No. 08/710,806 entitled "Optical Apparatus for Inspecting Laser Texture," filed on the same day as the present application, and having a common assignee therewith, describes the use of an interferometer configured to measure the profile of textured spots on a disk in comparison to an adjacent flat surface.

A co-pending U.S. application, Ser. No. 08/710,818 entitled "Apparatus for Optical Differential Measurement of Glide Height Above a Magnetic Disk," filed on the same day as the present application, and having a common assignee therewith, describes the use of an interferometer to measure changes in the glide height of a simulated magnetic head above a magnetic disk surface under test.

BACKGROUND OF THE INVENTION

1. Field of the Invention

This invention relates to an apparatus and method for acquiring and analyzing data from an interferometer, and, more particularly, to a method for analyzing the relative height of adjacent points on a surface imaged by an interferometer as the surface is moved in a scanning motion.

2. Background Information

Semiconductor wafers and magnetic disks, such as those used to store data in computer systems, have become very sensitive to surface flatness and other parameters determining surface quality. The surfaces of such devices need to be inspected with a high degree of accuracy for anomalies at a very high throughput rate to match the capabilities of the equipment used to manufacture such devices.

Thus, surface profilers have become key instruments used in the manufacture of such devices, being widely used to study surface topography, structure, roughness, and other characteristics. Surface profilers are categorized into a first class of instruments, providing contact measurements with a probe that physically contacts the surface being measured, and a second class of instruments, providing non-contact measurements without physically contacting the surface being measured. In many applications, non-contact measurements are strongly preferred to avoid contamination and mechanical damage to the surface being measured, and to allow inspection at a high surface speed.

An example of an instrument providing non-contact surface measurements is a surface profile interferometer, which is particularly used for determining the roughness of a surface or the height of a step change in the thickness of a part being measured. Such a step change may be caused, for example, by the application of a metal film to a substrate in the manufacture of a printed circuit board or an integrated microcircuit. In general terms, an interferometer is an optical instrument in which two beams of light derived from the same monochromatic source are directed along optical paths of different length, in which the difference in length determines the nature of an interference pattern produced when the light beams are allowed to interfere. Since the beams of light are derived from the same monochromatic source, they are identical in wavelength. At equal path distances from the source, they are also in phase with one another. Phase differences between the beams therefore result only from differences in path length.

The phenomenon of light wave interference results from the mutual effect of two or more waves passing through the same region at the same time, producing reinforcement at some points and neutralization at other points, according to the principle of superposition.

With a photoelectric shearing interferometer, the height of a step change in a test surface may be measured using polarized light passed through a slit, through a Wollaston prism, and through a microscope objective lens, to form two images of the slit, with one image on each side of the step change. The beams reflected by the test surface pass through the lens and the prism, with an image being formed by two orthoganally polarized beams. The phase difference between these beams, which is determined by the height of the step, may be measured by the linear movement of a weak lens in a lateral direction (transverse to the beam) until the phase difference is exactly cancelled, as determined by the use of an electrooptic modulator, an analyzer, a photomultiplier, and a phase-sensitive detector, which are used together to detect the phase equality of the two interfering beams. The accuracy of the system depends on the precision to which the linear movement of the weak lens can be measured. Thus, a difference in phase between two orthogonal polarizations is measured, with the beams laterally displaced by the Wollaston prism, so that the system is not a common-path interferometer.

The Wollaston prism makes use of the phenomenon of double refraction or birefringence, through which a crystal of a transparent anisotropic material refracts orthogonally polarized light beams at different angles. Crystals such as calcite, quartz, and mica exhibit this property. A Wollaston prism includes two wedge-shaped segments held together with adjacent polished surfaces extending along a plane at an oblique angle to the optical axis of the device. The outer surfaces of the Wollaston prism lie along planes perpendicular to the optical axis of the device. The two segments of the Wollaston prism are composed of a birefringent material, with the crystal axes of the material lying perpendicular to each other and to the optical axis of the device.

For example, if a beam of light consisting of two sub-beams polarized orthogonally to each other is directed along the optical axis of the device to a Wollaston prism, the two beams will not be refracted at the initial surface of the prism, since it lies perpendicular to the direction of both beams. However, when the two beams reach the oblique surfaces inner surfaces of the two segments of the prism, refraction will occur, with the two beams being refracted at different angles because of the birefringence of the material of which the prism segments are composed. When the two beams reach the opposite external side of the prism, they are again refracted.

While the above discussion describes a Wollaston prism comprising two wedges of birefringent material, it is possible and often advantageous to form a prism of this kind using three or more such wedges, joined at two or more oblique planes. When this is done, the outer surfaces of the prism remain perpendicular to the optical center of the device.

Thus, a number of methods have been developed for using interferometers to provide accurate measurements of very small surface features. However, since these methods are based on rather elaborate and painstaking processes in which a very small surface area is held in place to be viewed through an interferometer, they are difficult to apply to the materials of a mass production process making, in large volumes, parts which would benefit from inspection by means of interferometry.

What is needed is a way to apply a scanning process allowing a relatively large test surface to be examined without stopping for the measurement of individual areas, while providing quantitative data on step changes and on the slope of defect walls in real time during the scanning process.

DESCRIPTION OF THE PRIOR ART

U.S. Pat. No. 5,469,259 describes an interferometer provided with a light source forming a first collimated beam shaped to illuminate an area and a second collimated beam shaped to illuminate a narrow line. Both of these beams are split into orthogonally-polarized sub-beams, which are diverted outward and inward within a compound Wollaston prism. The images of these beams are focussed on a test surface through an objective lens, with a real splitting point being projected to the rear focal plane of the objective lens. With light reflected off the test surface and projected back through the compound Wollaston prism, interference patterns are generated on the surface of a line sensor, which is typically used with illuminated narrow lines split by the compound prism and projected onto a moving test surface, and on the surface of an area sensor, which is typically used with area illumination projected onto a stationary test surface. Autofocus and automatic phase angle correction servomechanisms are also provided within the interferometer.

SUMMARY OF THE INVENTION

In accordance with one aspect of the invention, there is provided inspection apparatus for inspecting the surface of a sample. The apparatus includes a wide scanning interferometer determining the presence of surface defects, a narrow scanning interferometer determining profiles of individual surface defects located by the wide scanning interferometer, and a mechanism for establishing relative motion between the sample and the interferometers, with the surface moving adjacent to the interferometers.

DETAILED DESCRIPTION

Figure 1:
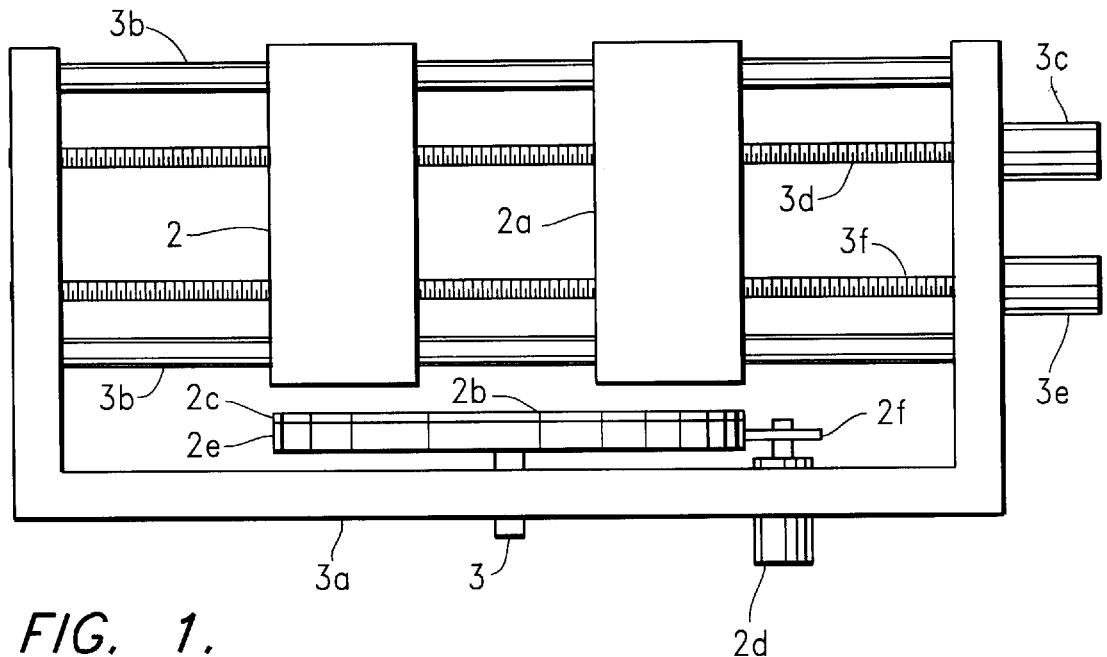
FIG. 1 is an elevational view of optical inspection apparatus built in accordance with the present invention.

FIG. 1 is an elevational view of optical inspection apparatus built in accordance with the present invention. In this apparatus, a wide-scanning interferometer 2 and a narrow-scanning interferometer 2a are independently moved adjacent a surface 2b being inspected. In this example, the surface 2b is an upper surface of a disk 2c being rotated by a motor 2d driving a turntable 2e by means of a wheel 2f. The wheel 2f is rotatably mounted at a shaft 3 in a framework 3a. Both interferometers 2, 2a are moved on a pair of rails 3b in a direction which is radial to the disk 2c. The wide-scanning interferometer 2 is moved by an upper drive motor 3c turning an upper leadscrew 3d, while the narrow-scanning interferometer 2a is moved by a lower drive motor 3e turning a lower leadscrew 3f.

Using this apparatus, the wide-scanning interferometer 2 is used to locate defects in the surface 2b, while the narrow-scanning interferometer 2a is used to produce actual profiles of the defects found. In a preferred version of this invention, the wide-scanning interferometer forms an interferogram along a linear CCD array, with bright areas corresponding to defects, whether raised of lowered from the main surface 2b. As the disk 2c continues to spin, the narrow-scanning interferometer 2a is driven to the radius at which each such defect is found. This process may be carried out with the wide-scanning interferometer 2 completely traversing the surface 2b, storing the locations of defects found, followed by the use of narrow-scanning interferometer 2a to generate the defect profiles. Alternately, both interferometers may be used simultaneously, with the narrow-scanning interferometer being driven to defects as soon as possible after they are found.

Figure 2:
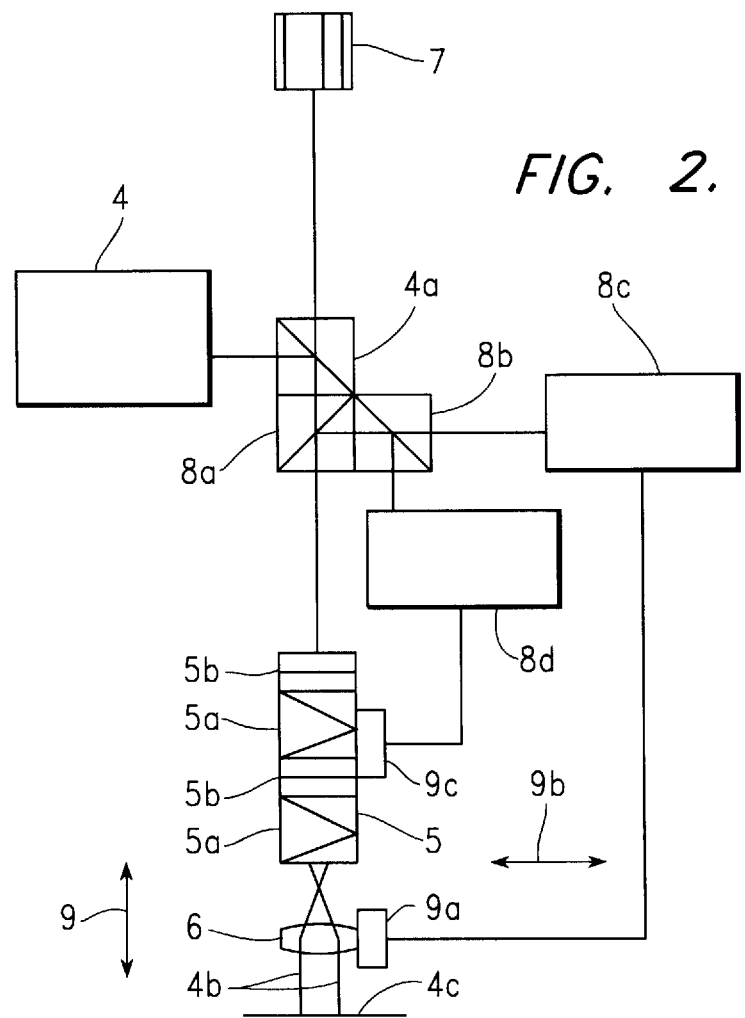
FIG. 2 is a schematic elevation of a wide-scanning interferometer in the apparatus of FIG. 1.

FIG. 2 is a schematic elevation of an interferometer which may be used as the wide-scanning interferometer 2 of the present invention. U.S. Pat. No. 5,469,259 describes this device in a version having both a scanning mode and a static mode of operation. For use in the present invention, only the scanning mode is required. The interferometer 2 is a common mode shearing type, in which a beam from a laser light source 4, directed downward by a beamsplitter 4a, produces a pair of sheared sub-beams 4b, both of which are incident on a surface 4c being inspected. The sheared sub-beams 4b are produced by a compound Wollaston prism assembly 5, including Wollaston prisms 5a and half-wave plates 5b. The objective lens 6 forms an interferogram of a portion of the surface 4c on a line scan sensor 7, which is used for the acquisition of surface data as the surface 4c is moved relative to the interferometer 2.

A portion of the return beam is split off by a beamsplitter 8a, to be divided by another beamsplitter 8b between a focus detector 8c and a phase detector 8d. An autofocus feature is thus provided, as focus detector 8c drives the objective lens 6 in the directions of arrow 9, by means of a piezoelectric actuator 9a, to maintain focus. Phase detector 8d drives the compound Wollaston prism assembly 5 in the directions of arrow 9b by means of a piezoelectric actuator 9c, preferably maintaining darkfield conditions, in which the interferogram formed at linear CCD array 7 is dark in areas corresponding to flat portions of surface 4c and bright in areas corresponding to defects in the surface 4c.

A more complete description of this apparatus and its operation is found in U.S. Pat. No. 4,469,259.

Figure 3:
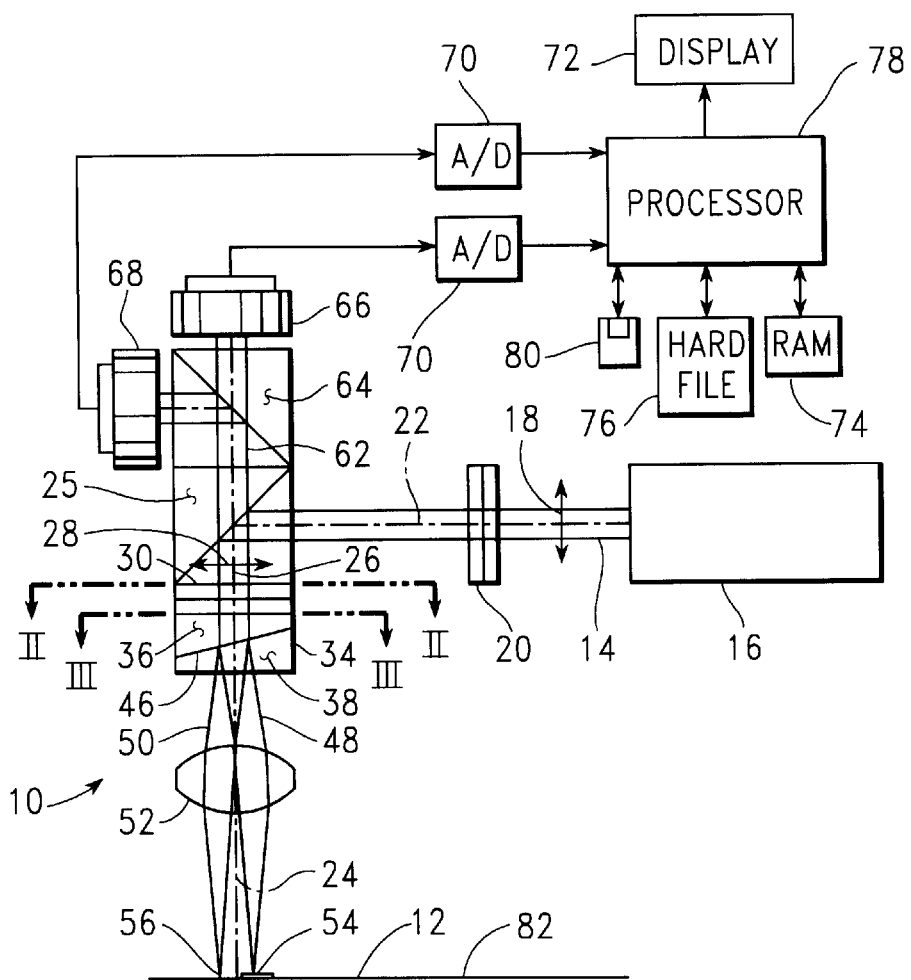
FIG. 3 is a schematic elevation of a narrow-scanning interferometer in the apparatus of FIG. 1.

FIG. 3 is a schematic elevation of the narrow scanning interferometer 2a. Within this apparatus, a test surface 12 is illuminated from a beam 14 projected from a laser unit 16. A laser unit having an output beam with a wavelength of 532 nanometers has proven to be satisfactory in this application. This beam leaves the laser unit vertically polarized, as indicated by arrow 18. A half-wave plate 20 is rotated about the axis 22 of the laser beam 14 to provide a fine adjustment of the vertical polarization of the laser beam 14 projected therethrough. After passing through half-wave plate 20, a portion of the laser beam 22 is deflected downward, along an optical axis 24 of the interferometer 2a, within a non-polarizing beamsplitter 25. A portion of the laser beam 14 is wasted, being transmitted through the beamsplitter 25 instead of reflected therein. The downward-directed reflected laser beam 26, which is horizontally polarized as indicated by arrow 28, is projected through a second half-wave plate 30.

Figure 4:
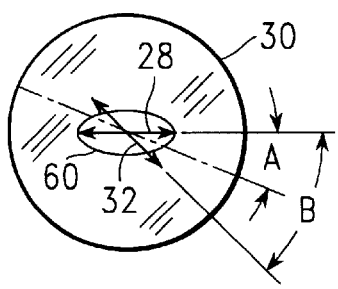
FIG. 4 is a schematic plan view of a half-wave plate in the interferometer of FIG. 3, showing the polarization orientations of beams passed therethrough.

FIG. 4 is a schematic plan view of the second half-wave plate 30, taken as indicated by section lines II—II in FIG. 3, to show the polarization orientations of laser beams projected therethrough. The transmission of linearly polarized light through a half-wave plate results in the rotation of the angle of polarization through an angle which is twice the angle between the direction of polarization and the crystal axis of the material composing the half-wave plate. In the example of half-wave plate 30, the crystal axis is at a 22.5 degree angle, indicated as angle A, from the polarization direction, indicated by arrow 28, of the downward-reflected beam 26 (shown in FIG. 3). Therefore, in passing through half-wave plate 30, the direction of polarization of this laser beam is rotated through a 45-degree angle, indicated as angle B, to have the orientation indicate by arrow 32.

Figure 5:
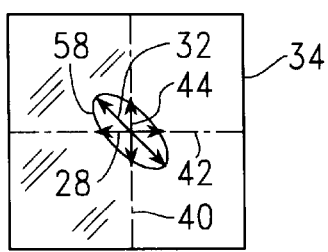
FIG. 5 is a schematic plan view of a Wollaston prism in the interferometer of FIG. 3, showing the polarization orientations of beams passed therethrough.

FIG. 5 is a schematic plan view of a Wollaston prism 34, directly below the second half-wave plate 30, taken as indicated by section lines III—III in FIG. 3, to show the polarization of laser beams traveling through the upper portion of the prism 34.

Referring to FIGS. 3 and 5, the Wollaston prism 34 is composed of a pair of wedge-shaped segments 36, 38 of crystalline material having crystal axes 40, 42 which are perpendicular to one another and to the optical axis 24 of the interferometer 2a. Thus, the downward deflected laser beam 26 enters the Wollaston prism 34 being polarized in a direction at a 45-degree angle from the optical axis of the upper wedge-shaped segments 36, and is therefore decomposed into a pair of sub-beams of equal intensity, polarized in the mutually-perpendicular directions indicated by arrows 28, 44. Since the crystalline material forming each segment 36, 38 of the Wollaston prism 34 is birefringent, refracting beams polarized at different angles in different directions, the two sub-beams travelling downward therethrough, being polarized perpendicularly to one another, as indicated by arrows 28, 44, are refracted differently at the interface 46 between the segments 36, 38. In general, the Wollaston prism separates the two sub-beams exiting its lower surface by a deviation angle, which is a function of the wavelength of the laser beam, the indices of refraction of the materials of which the wedge-shaped portions 36, 38, and the angle at which the interface surface 46 is sloped.

In general, a Wollaston prism may be composed of a number of wedge-shaped segments, from a single segment up to three or more segments. In a Wollaston prism having one or two segments, the sub-beams diverge from a surface, such as interface surface 46, which is called a split point. In a Wollaston prism having three or more segments, the sub-beams are typically brought back together, to cross one another at a cross-over point between the Wollaston prism and the objective lens. If there is no cross-over point, the split point is in the back focal plane of the objective lens. If there is a cross-over point, the final cross-over point is in the back focal plane of the objective lens.

In this way, a right sub-beam 48 having a first direction of polarization and a left sub-beam 50, having a direction of polarization perpendicular to that of right sub-beam 48 are formed. Both of these sub-beams 48, 50 pass through an objective lens 52, being focussed on test surface spots 54, 56, respectively. After reflecting off the test surface spots 54, 56 the sub-beams 48, 50 return upward through objective lens 52 and Wollaston prism 34, being recombined at the upper wedged-shaped segment 36 of the prism 34. During the process of reflection off the spots 54, 56. the directions of polarization remain as indicated by arrows 28, 44.

In the example of FIG. 3, test surface spot 54 is raised above the level of test surface spot 56. Since the distances travelled by the sub-beams 48, 50 are different, the times required for projection and reflection from the test spots 54, 56, respectively, are different, producing a phase-shift between the two sub-beams 48, 50 as they are reflected back to the Wollaston prism 34. When these reflected sub-beams are recomposed within the Wollaston prism 34, due to this phase shift, they form an elliptically polarized beam, having major and minor axes extending at 45-degree angles to the crystal axes 40, 42 of the materials making up the Wollaston prism 34. In FIG. 5, the polarization of this recomposed beam is indicated by an ellipse 58.

Referring to FIGS. 4 and 5, as the recomposed beam is transmitted upward through half-wave plate 30, its elliptical polarization is rotated to have major and minor axes extending in the direction of arrow 28 and in the direction perpendicular thereto, as indicated by an ellipse 60. The relative intensities along the major and minor axes of ellipse 60 are determined by the phase-shift between the sub-beams 48, 50 returning after reflection from the test spots 54, 56.

Referring again to FIG. 3, the recomposed beam is transmitted upward from half-wave plate 30 into the non-polarizing beamsplitter 25, with the transmitted portion 62 of this recombined beam being used for subsequent measurements, as the portion of this beam reflected within the beamsplitter 25 is discarded. The elliptical polarization indicated by ellipse 60 in FIG. 4 is retained. The transmitted portion 62 of this beam is next split within a polarizing beamsplitter 64, with a portion of the beam 62 polarized in the direction indicated by arrow 28 being transmitted into a first photodetector 66, while a portion of the beam 62 polarized in the direction of arrow 44 (shown in FIG. 5) is reflected into a second photodetector 68.

The output of each photodetector 66, 68 is provided as an input to a corresponding analog to digital convertor 70, which in turn provides an input to a computer processor 72. This processor 72 is a conventional device connected to conventional devices, such as a system memory 74, a hardfile 76, and a display unit 78. Programs for execution within the processor 72 are loaded into memory 74 from a diskette 80.

Referring again to FIGS. 1 and 2, the operation of the apparatus as the wide-scanning interferometer 2 is used to acquire the locations of defects will now be described. In a typical application of the apparatus, the disk media of a hardfile is measured to determine smoothness to a few nanometers. In accordance with the present invention, an automated procedure is provided for first scanning the disk using the line scan CCD sensor 7, determining where defects are detected in the disk surface. The location of each such defect is stored for the subsequent development of a profile by means of the narrow scanning interferometer 2a.

The basic technique of measurement with wide-scanning interferometer 2 uses laser darkfield shear length interferometry, yielding darkness corresponding to the smooth areas while defects appear as spots of brightness. In this measuring process, the disk 2c is scanned in a spiral motion, rotating with turntable 2e as the interferometer 2 is also driven in a linear motion by motor 3c. The surface 2b of the disk 2c is illuminated with the interferometer. The line scan CCD sensor 7 follows this scan, recording bumps or pits in the disk surface as bright spots. Fortunately, the vast majority of a typical disk is recorded as blackness, indicating that the disk is flat within desired limits. For example, a 95-mm disk produces approximately 460 Mbytes of data, almost all of which are typically null data without value.

Figure 6:
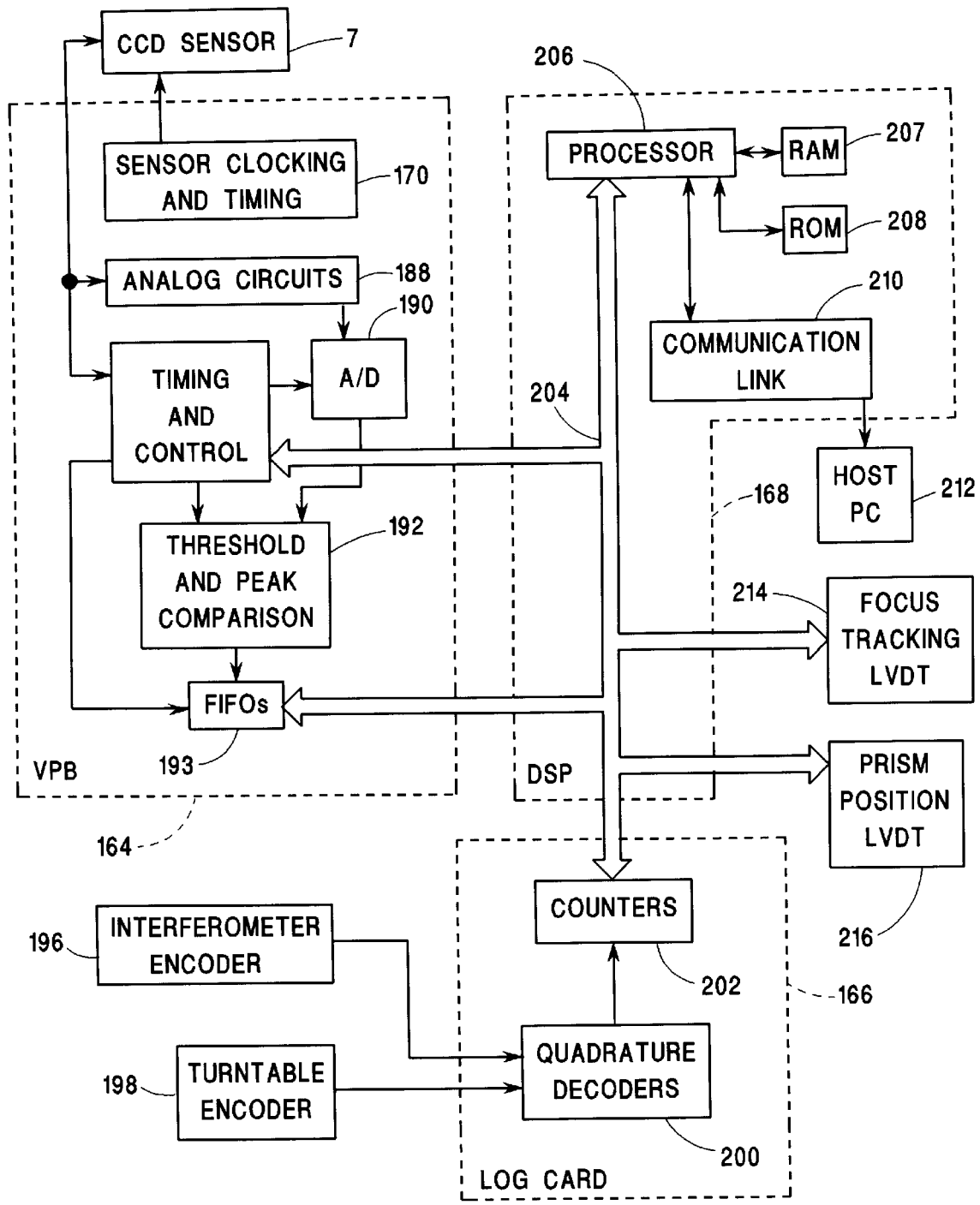
FIG. 6 is a block diagram of a video preprocessing system for acquiring data from a line scan CCD sensor within the wide-scanning interferometer of FIG. 2.

FIG. 6 is a block diagram of a video preprocessing system, which sorts through this data, arriving at a rate of 20 million samples per second from the output of CCD line scan sensor 7. This system discards the null data, storing the valuable data with tags that locate each datum to a point on the disk surface. The video preprocessing system consists of three main parts—a video processor board (VPB) 164, which powers and clocks line scan sensor 7 while processing and returning data from the sensor 7; a position logging card (log card) 166, which reads the outputs indicating the rotational position of turntable 2e and the linear position of carriage 159; and a digital signal processor (DSP) 168, which processes data from the VPB 164 and the log card 166 to produce a location map of detected features.

Figure 7:
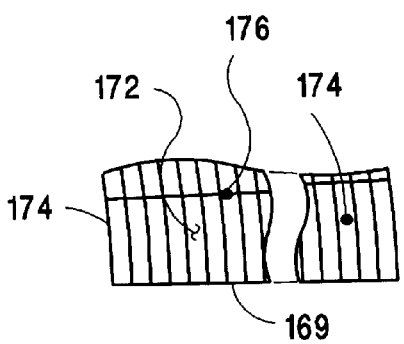
FIG. 7 is a schematic elevational view of a line scan CCD sensor within the wide-scanning interferometer of FIG. 2, which further indicates a portion of the surface examined during a single video line scan of a test sample by this sensor.

FIG. 7 is a schematic elevational view of line scan CCD sensor 7 within the wide-scanning interferometer 2 of FIG. 2, with additional indications of a portion of the surface examined during a single video line scan of a test sample by this sensor. The sensor 7 includes 1063 pixel elements 169, of which 1024 are active pixel elements, each of which measures the illumination level of an interferogram corresponding to an area which is 0.6 microns wide. Thus, the interferogram of a portion of the test surface 16, having a width of 614 microns, is viewed by the line scan CCD sensor 7.

Referring to FIGS. 6 and 7, the VPB 164 functions as a controller for the CCD sensor 7, powering and clocking the sensor 7 as well as processing returning video data. In sensor clocking and timing circuits 170, the VPB 164 generates a 20 MHz (megahertz) clock with a line synch pulse every 1063 clock cycles. This synch pulse causes the CCD elements within the sensor 7 to be dumped to their associated shift register and to begin transferring data to the VPB 164. During the scanning process, a scan of a video line, providing data from each of the 1063 pixels, occurs with each clock pulse from the sensor clocking and timing circuits 170. Since these pulses occur at a rate of 20 MHz, the time between pulses is 50 nanoseconds, and the line synch pulse between line scans occurs every 53.15 milliseconds.

Referring again to FIG. 2, the wide-scanning interferometer 2 produces two polarized, illuminated lines on the surface being examined. Therefore, each measurable defect in this surface results in two images, or brightspots in the darkfield, being sequentially detected through the line scan CCD sensor 7. These two lines are separated by 60 microns, the shear distance of the interferometer 2.

Since the timing between video line scans is held at 53.15 milliseconds, the distance travelled by the surface 2b being examined between video lines is determined by the speed at which the surface is driven. Preferably, this distance travelled is set at a submultiple of the shear distance, so that the two images arising from a single defect are more easily identified and related to one another. In the present application of examining hardfile media, the distance is preferably set to 30 microns, or half the shear distance. Different types of surfaces are most effectively examined with this distance set at different submultiples of the shear distance. With 53.15 milliseconds between video scans, the desired distance of 30 microns is obtained by setting the velocity at 0.5644 meter/second. Under these conditions, the line scan in which the second image of a defect is detected is usually the second line scan behind the line scan in which the first image of the defect is detected. In the present application, this velocity is held at a constant level while examining a spiral pattern on a disk-shaped surface by decreasing the angular velocity of the turntable 2e (shown in FIG. 1).

Referring again to FIG. 7, this scanning process divides the surface being examined into 1024 pixels 172, each of which represents the surface conditions of a spiral arc 0.6 microns wide and 30 microns long. The entire video scan represents the surface conditions of a spiral arc 174, which is 614 microns wide and 60 microns long. In the CCD array of sensor 7, there are 1063 pixel elements, 1024 of which are active, containing valid data. The remaining pixel elements provide control and video information that is not valid data. The VPB 164 (shown in FIG. 6) ignores these non-informative pixels and examines the active pixels.

Since only one output is provided from each pixel element during each video line scan, an area integration is produced within each pixel 172. That is, the brightness levels associated with two or more defects 174 in the same pixel are added to produce the output of that pixel. Nevertheless, this method of scanning produces valuable results, particularly since a single measurable defect, or multiple defects, within a particular pixel is a relatively rare event. A further form of integration is provided by the process when, for each line scan having one or more detected defects, the intensity of the pixel having the greatest intensity is stored as a single maximum intensity level associated with the line scan.

On the other hand, a single defect 176 may occur at a boundary between pixels within sequentially adjacent video line scans. This occurrence does not present a problem, except that, due to the effect of area integration within each pixel 172, the resulting output for each of the pixels may be below the threshold level, so that a defect which should be detected is missed. To avoid this occurrence, the process of the present invention examines the maximum intensity levels of adjacent integrals, determining if their combination should result in the detection of a defect.

Figure 8:
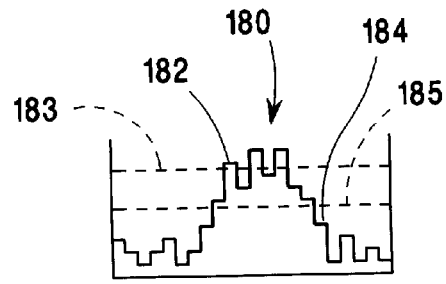
FIG. 8 is a graphical view of the output of a line scan CCD sensor of FIG. 7.

FIG. 8 is a diagram of the output signal from the line scan CCD sensor 7, in which the individual levels 178 indicate the intensity output levels of individual pixel elements 169 (shown in FIG. 7), as the intensities of these pixel elements are sequentially clocked out at the clock rate of 50 MHz. A measurable level of noise associated with this signal causes relatively small differences in the intensities of adjacent pixel elements. A generally bell-shaped curve 180 indicates that a defect is being detected. This shape is determined both by the size of the defect and by the fact the optical system of interferometer 2 cannot be perfectly focussed. The detection of a defect is begun with the first pixel element output 182 above a beginning threshold level 183. The detection of a defect is then ended with the first pixel element output 184 below an ending threshold level 185. Thus a differential zone of output voltages, in which the detection of a defect may be begun but not ended, is provided between the two threshold levels 183 and 185. If the beginning and ending threshold levels were instead at the same level, the presence of a single defect having an intensity near the threshold level would cause the false detection of several defects, as the noise on the signal would turn the detection process on and off. This gap between the threshold levels 183 and 185 may be implemented by storing the two threshold levels. Alternately, a single threshold level, corresponding to the ending threshold level 185 may be used for both comparisons, if certain low-order bits from the digital code representing the beginning intensity signal are ignored, forcing this signal to be actually higher to start the detection of a defect.

Referring again to FIG. 6, as well as to FIG. 8, data coming into VPB 164 passes through analog circuitry 188, to be digitized in an A/D convertor 190, before being delivered to a video processing section 192, where the data is compared to the threshold levels 183 and 185. If all the data from an individual video scan is below the beginning threshold level 183, the intensity data is discarded, and a single, end of integral, code is sent at the end of the scan for synchronization, along with an indication of the maximum pel intensity of the video scan line.

Figure 9:
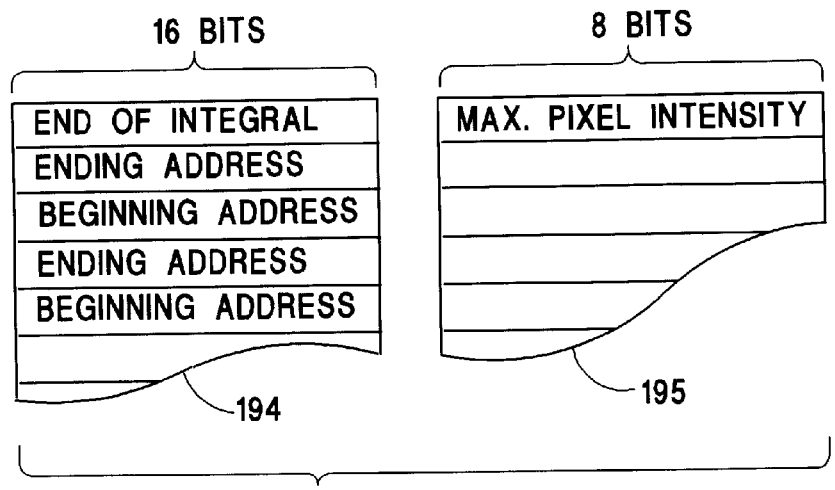
FIG. 9 is a schematic diagram of FIFO buffers within the preprocessing system of FIG. 6.

FIG. 9 is a schematic diagram of the FIFO registers shown as 193 in FIG. 6. These registers are composed of a 16-bit address register 194 and an 8-bit data register 195.

Referring to FIGS. 6–9, if the intensity level from a pixel element 169 beginning the detection of a defect exceeds the beginning threshold level 183, the video processing section 192 stores the pixel number of that pixel element 169 in address memory 194. For each pixel, regardless of whether the VPB state is above or below threshold level, the current maximum pixel intensity is compared to the current pixel intensity. If the current pixel intensity is greater, a new maximum pixel intensity is stored. If a data value falls below the ending threshold level 185, the pixel number of the pixel element 169 providing the data value is stored as the ending address in address register 194. If another defect is detected, this process is repeated. With the synch pulse from sensor clocking and timing circuits 170, an all-zeros end of integral marker is recorded in the address register, and the maximum pixel intensity stored internally by the video processing section 192 is stored in the data register 195. Thus, for each transition of the intensity signal above the beginning threshold level, starting and ending pixel addresses are stored in address buffer 194. For each video scan, or integral, having such a transition, a maximum pixel intensity is stored in the data register 195. The starting and ending addresses provide the width of each feature and the distance offset from the edge of the video scan. The peak video value, along with this width, provide information concerning the overall size of the feature.

Referring again to FIG. 6, the log card 166 is used, in conjunction with the pixel addresses from VPB 164, to determine the position of a feature on the disk. The log card records the position of the interferometer 2 and of the turntable 2e as the disk 2c is driven to inspect a spiral pattern on the test surface 16 (all shown in FIG. 1). This data is obtained from optical position encoders 196 and 198, providing the position of the interferometer 2 and turntable 2e, respectively. Within log card 166, quadrature decoders 200 decode the signals from encoders 196 and 198 to make a relatively coarse determination of the location of the interferometer 2 and turntable 2e, while counters 202 count pulses from the encoders to make a fine determination of these locations. Each time VPB 164 sends a synch signal indicating that a new video line has just begun, the log card 166 is triggered to latch the radial (interferometer) and rotational (turntable) positions. When the pixel address is added to the radial position, the resulting data provides the location of the feature on the disk, in the form of a radius and an angle theta. In this way, a position metric is produced to be stored with the feature data. This function is critical to the video preprocessing system, since the position of data is otherwise lost as the null data is discarded.

Both VPB 164 and log card 166 attach to DSP 168, by means of DSP bus interface 204. DSP 168 includes a processor 206, random-access memory (RAM) 208, read-only memory (ROM) 210, clocks and system timing, analog to digital converters, and a communication link 210 to a host personal computer (PC) 212. The DSP 168 synchronizes and controls operations of the VPB 164 and log card 166, producing data for each detected feature, consisting of the position, magnitude, and width of the feature. The DSP 168 also combines information about features that span sequentially adjacent video scan lines, producing composite feature data.

Referring again to FIG. 2, as previously discussed, the objective lens 6 is moved in the directions of arrow 9 by means of a piezoelectric actuator 9a, as part of an autofocus system responding to variations in the thickness of the part being examined, such as the disk 2c. Also, Wollaston prism assembly 5 is moved in the direction of arrow 9b by an automatic system driving an actuator 9c to maintain the phase angle difference between the two polarized light beams striking the surface being examined. In the type of system operation now being described, this phase angle difference is controlled to maintain a darkfield.

Referring again to FIG. 6, a Linear Variable Displacement Transducer (LVDT) 214 tracks the position of objective lens 6 as it is varied with piezoelectric actuator 9a, and a prism position LVDT 216 tracks the position of the Wollaston prism assembly 5 as it is varied by the operation of actuator 9c. Since these movements are made in response to changes in the location or angle of the surface being examined, they provide an indication of the general flatness or runout of the disk. Therefore data from these sensors 214 and 216 is also collected by the DSP 168.

The DSP 168 packs all of this data, forwarding it to the system host computer 212, where maps of features and of parameters, such as disk runout, are produced. On a typical high-quality disk blank having fewer than ten detectable features, the quantity of data sent to the host computer is a very small fraction of the data sent from CCD sensor 7 and sensors 214 and 216. With this system, instead of the 450 Mbytes which could be required without such techniques, a few hundred bytes are used to mark and identify all features of interest.

Figure 10:
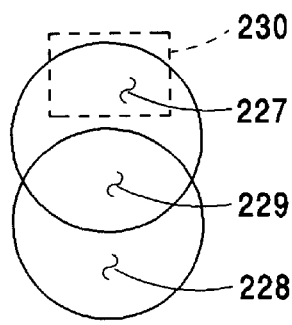
FIG. 10 is a schematic elevational view of areas of significance in an interferogram produced at an area array CCD sensor in the wide-scanning interferometer of FIG. 2.

FIG. 10 is a schematic diagram showing areas of interest in an interferogram which may be produced using static scan area CCD sensor 7. A first area 227 includes positive image information describing the defect. A second area 228 includes negative image information describing the defect. Since an overlapping area 229 includes both positive and negative images of the same defect, it cannot be used to provide valid data describing the defect. The dashed lines represent a bounding box 230 in which image information is gathered to learn various details concerning the defect. In order to assure that invalid data from the overlapping area 229 is not included in the data being considered, the center of bounding box 230 is placed at the second image resulting from the dual-line pattern from the linear scanning process of line scan CCD sensor 7.

Figure 11:
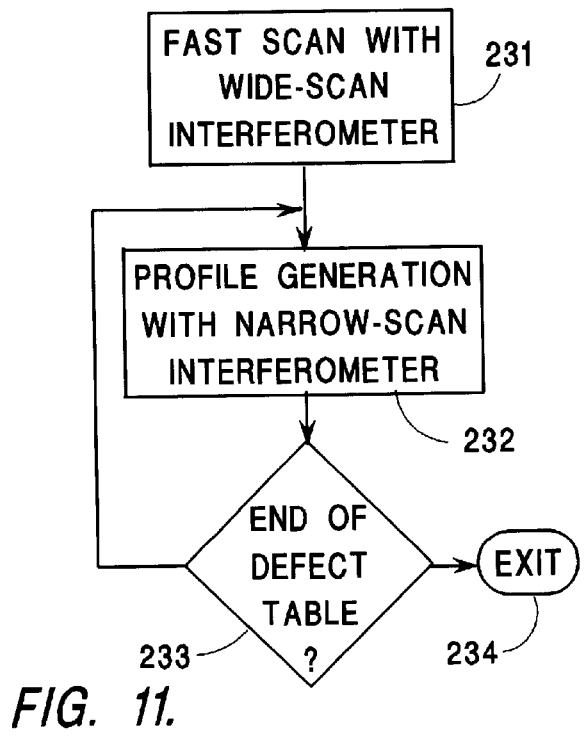
FIG. 11 is a flow diagram showing overall processes of the apparatus of FIG. 1.

FIG. 11 is a flow diagram showing the operation of the overall processes of the inspection system. First, as represented in step 231, a fast scan of the disk surface is performed at a constant linear velocity, using data generated from the line scan CCD sensor 7 with the various elements described above in reference to FIGS. 6–9. During this process, a defect table is developed, listing all of the defects found, together with their locations on the list. Following this scan, in step 232, the generation of a profile of each defect in the defect table is performed, using the narrow-scan interferometer 2a (shown in FIG. 3). When each such individual profile generating scan is completed, a test is made in step 233 to determine if the end of the defect table has been reached. If it has, the process is exited at 234; otherwise, the next defect from the table is examined in step 232. Alternately, the profile generation may begin when there are sufficient defects listed in the defect table, to continue simultaneously with the fast scan process.

Figure 12:
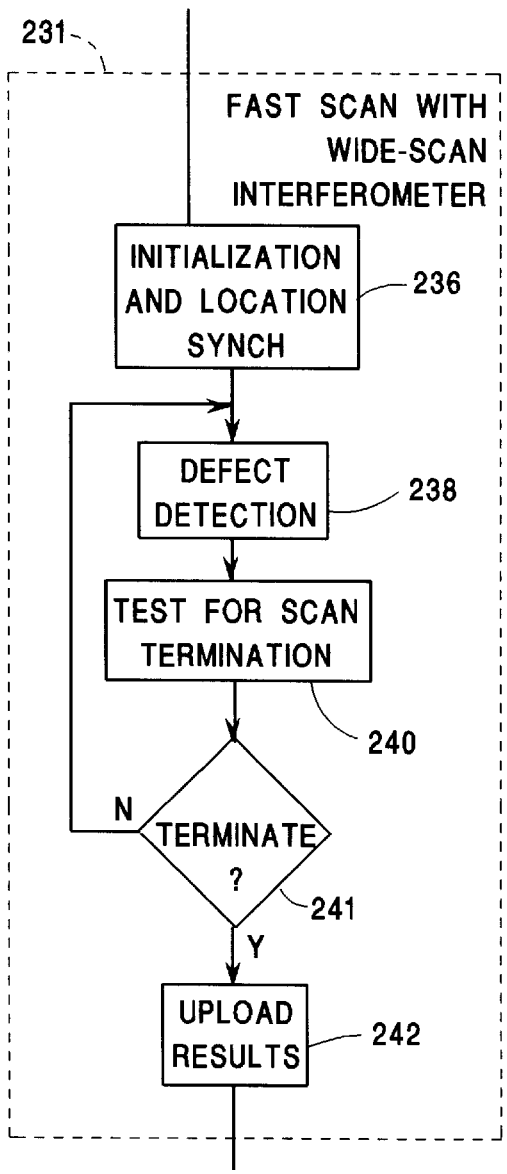
FIG. 12 is a flow diagram of a fast scan process of FIG. 11.

FIG. 12 is a flow diagram showing the operation of the fast scan process represented in step 231 of FIG. 11. In particular, this FIG. provides an overview of the operation of code running in the DSP 168. At the beginning of the fast scan process, in step 236, various circuits are initialized at the starting point of the scan. This initialization process will be discussed in detail in reference to FIG. 13. Then, within the active area of the disk, which is the portion of the disk to be examined, defects are detected in step 238. The defect detection process will be discussed in detail in reference to FIG. 15. In step 240, a test for scan termination is made when processor time is available with the results of this test being applied in step 241. For example, scan termination occurs if too many defects have been detected, indicating that the part being tested should be rejected without further testing, or if the detection process has moved off the active area. If scan termination occurs, in step 242, the results of the scan are uploaded to host computer 212 (shown in FIG. 6).

Figure 13:
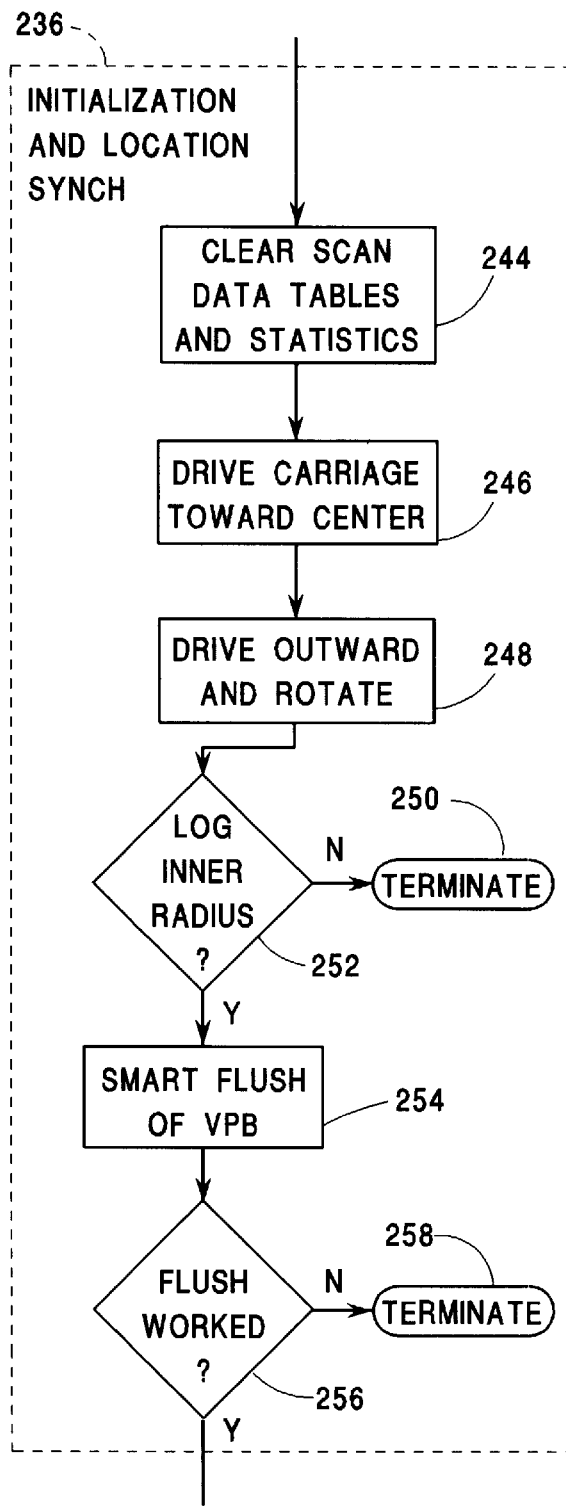
FIG. 13 is a flow diagram showing an initialization and synchronization process of FIG. 12.

FIG. 13 is flow diagram showing the operation of the initialization and synchronization process in step 236 of FIG. 12. Referring again to FIG. 1, as well as to FIG. 13, in step 244, the data tables and statistical values are cleared to eliminate values from a previous fast scan. Then, in step 246, the interferometer 2 is driven so that an area toward the center of the disk 2c from the inner radius of the active area is aligned for inspection. In step 248, the turntable 2e is brought up to rotational speed as the stage is driven outward toward a point at which the inner radius of the active area is aligned for inspection. If the inner radius is not logged, the process is terminated at 250 from step 252; otherwise, in step 254 a smart flush is performed on VPB 164 (shown in FIG. 6), resetting variables and synchronizing the operation of the VPB with data flowing into it from the line scan CCD sensor 7. If the smart flush process cannot be completed, as determined in step 256, the overall process is terminated at 258.

Figure 14:
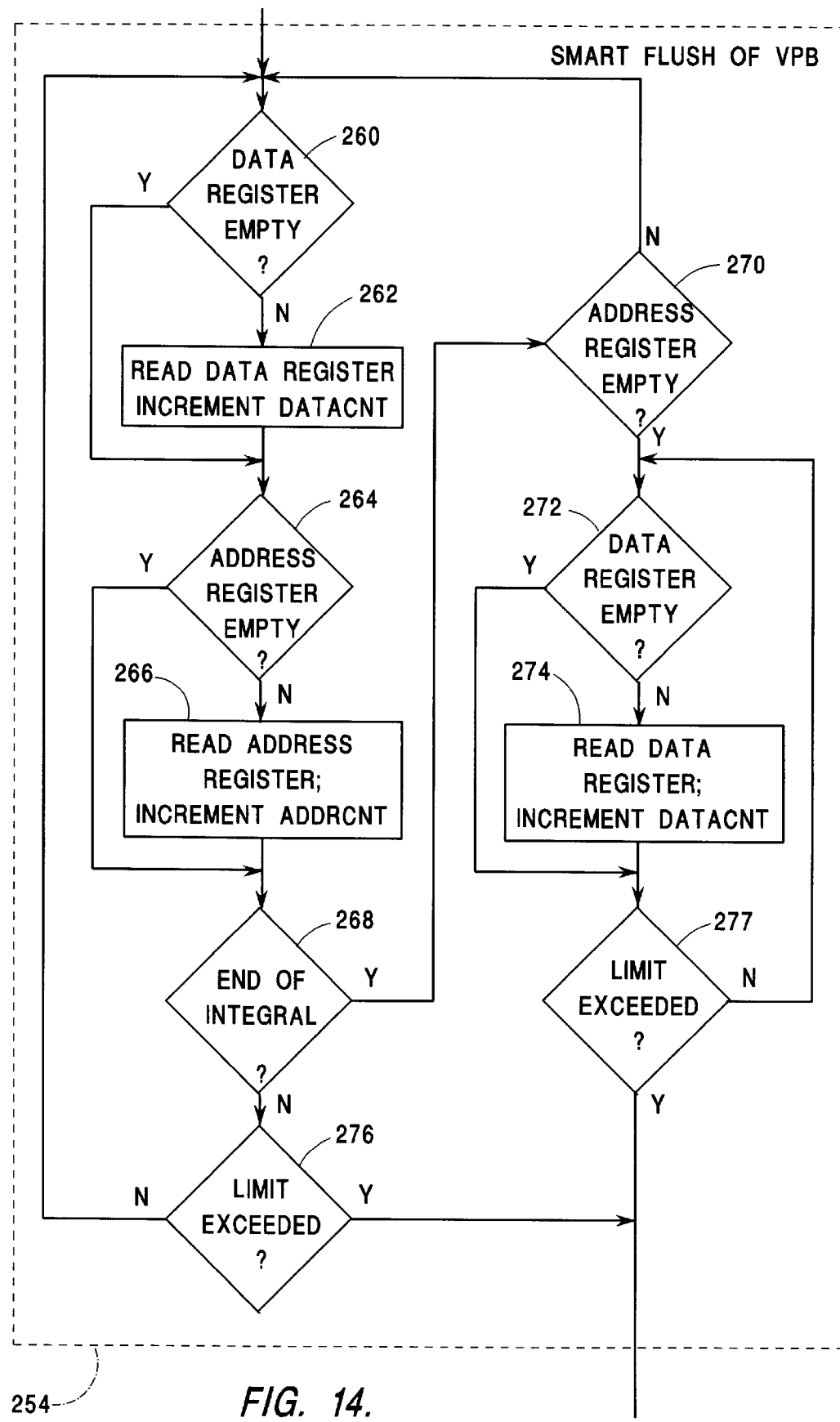
FIG. 14 is a flow diagram of a smart flush process of FIG. 11.

FIG. 14 is a flow diagram showing the details of the smart flush process occurring in step 254 of FIG. 11. In particular, this process clears the FIFO registers described in reference to FIG. 9. In step 260, the last position of data register 195 is checked to determine if it is empty, if it is not empty, this position is read in step 262, and the variable DataCnt is incremented. This variable, if it is at an excessive level, indicates an error condition occurred within the previous operation of the VPB, since the defect detection process of block 238 has not been able to keep up, emptying the data buffer as fast as it has been filled. Next, in step 264, the last position of address register 194 is similarly examined to determine whether it is empty. If it is not empty, this position is read in step 266, and the variable AddrCnt is incremented. This variable, if it is at an excessive level, similarly indicates that an error condition has occurred within the previous operation of the VPB, since the address buffer has not been emptied fast enough. The error conditions indicated by DataCnt and AddrCnt may be caused by a hardware failure, by the beginning threshold level 183 (shown in FIG. 8) being set too low, or simply by an especially bad disk 2c (shown in FIG. 1) displaying too many defects.

In any case, a determination is next made in step 268 of whether an end of integral (video line scan) condition has been indicated by an all-zeros address in address register 194. If an end of integral condition has occurred, the last position of the address register is again checked in step 270. If it is empty, the data register 195 is again checked in step 272. At this point, if the data register is empty, the VPB flush process has been completed, so step 254 is exited. If the data register is not empty, the last value is read in step 274, and DataCnt is incremented. In general, when a determination is made that one of these registers is not empty, the system reads the value and returns to repeat the determination. However, if one of the variables DataCnt or AddrCnt has reached a predetermined limit, as determined by testing at steps 276 and 277, the flush step is also exited, as there is no need to continue.

Figure 15:
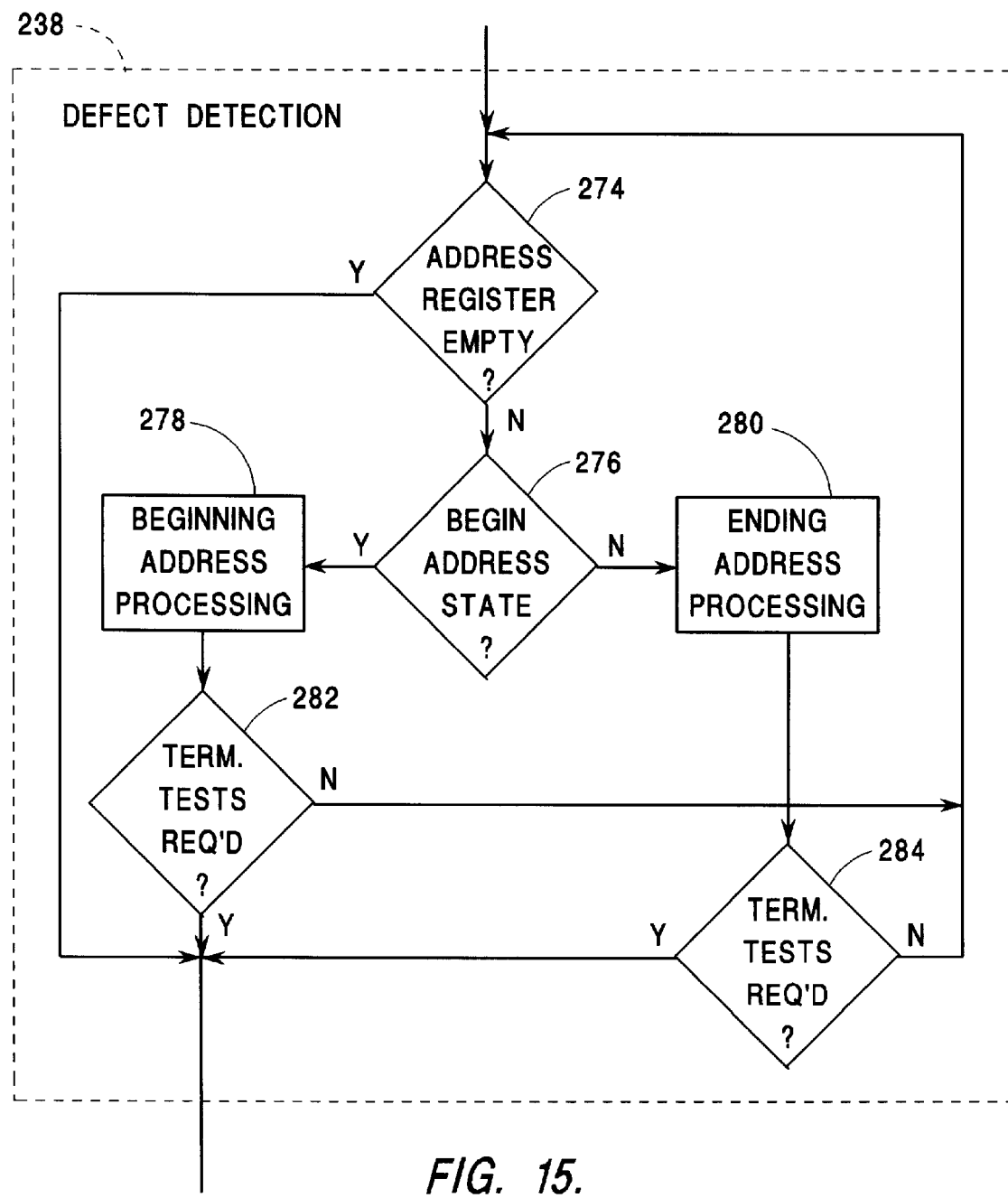
FIG. 15 is a flow diagram of a defect detection process of FIG. 12.

FIG. 15 is a flow diagram showing the operation of the defect detection process occurring in step 238 of FIG. 12. This is a process through which the DSP 168 (shown in FIG. 9) examines each defect for which data has been stored in the FIFO registers 194 and 195 (shown in FIG. 12). In step 274, a determination is made of whether the address register 194 is empty. If it is, there is no defect to detect, nor end of integral marker to process, so address processing is bypassed. Next, a determination is made, in step 276, of whether the next data in the address register 194 is a beginning address. After an End of Integral code, the next address (unless it is another line integral code) must be a beginning address. After a beginning address, the next address must be an ending address. From this point, the type of address toggles between beginning and ending, until an End of Integral code is reached. If the address is determined in this way to be a beginning address, the beginning address processing, which will be is explained in detail in reference to FIG. 16, occurs in step 278. If the system is not in the beginning address state, ending address processing, which will be explained in detail in reference to FIG. 17 occurs in step 280.

Referring again to FIG. 12, following the defect detection process, a test is made, in step 240, for scan termination. Thus, following beginning address processing in step 278, a test is made in step 282 to determine if the update count is at its limit. If it is, terminal testing is needed, so the system exits the defect detection process of step 238. If the update count is not at its limit, the address register is again checked at step 274, for the next data point. Similarly, after the ending address processing of step 280, a determination is made in step 284 of whether the defect table is full. If it is, terminal testing is needed, so the system exits the defect detection process of step 238. If the defect table is not full, the address register is again checked at step 274, for the next data point.

Figure 16:
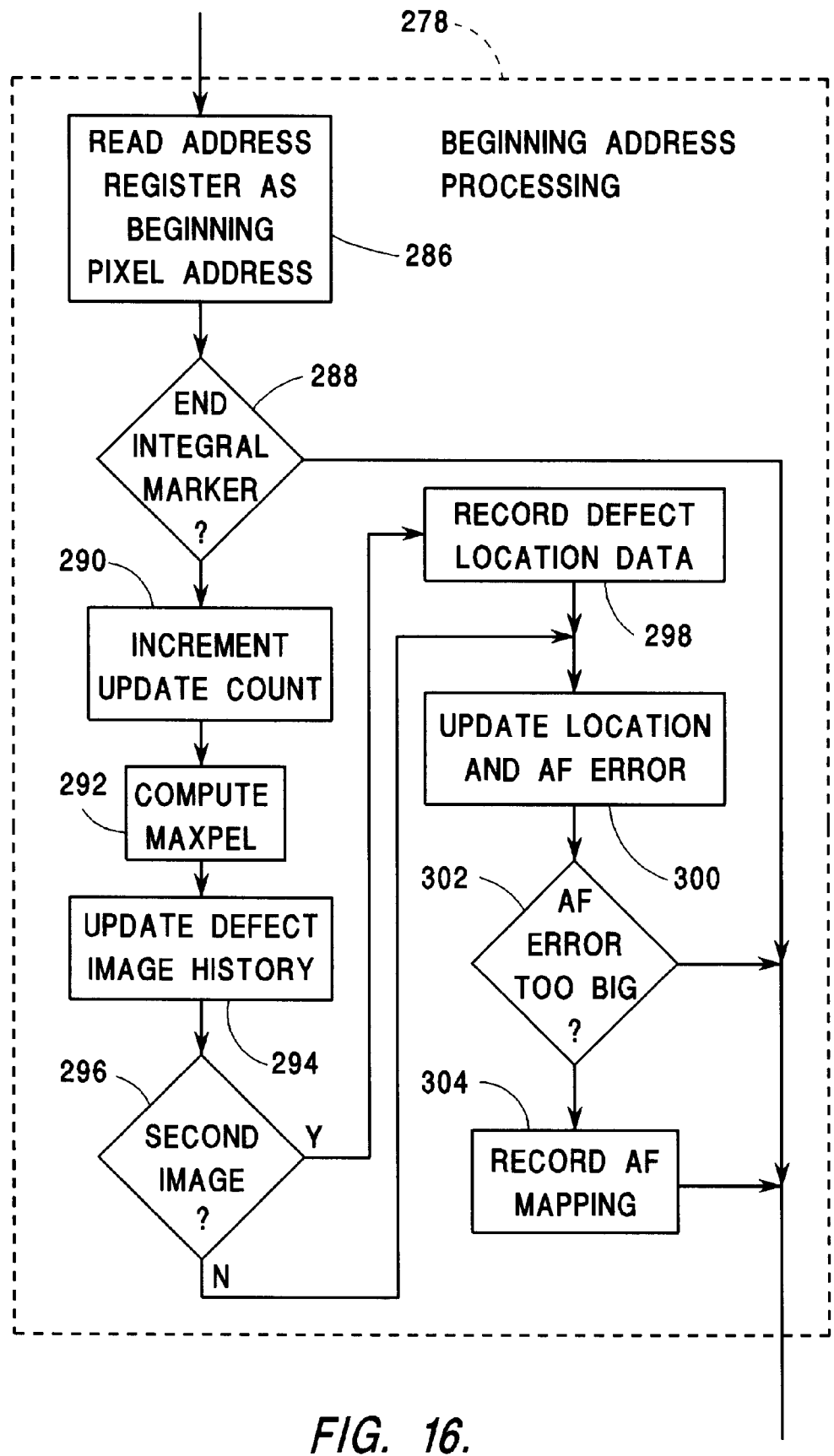
FIG. 16 is a flow diagram of a beginning address processing process of FIG. 15.
Figure 17:
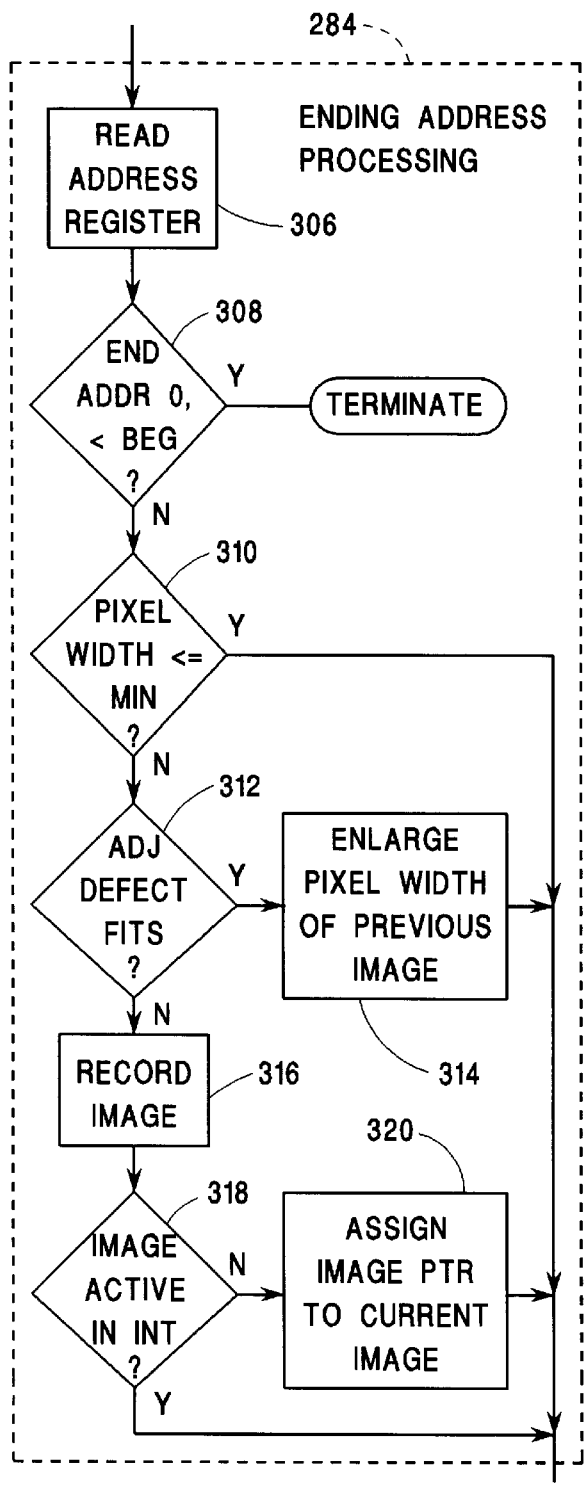
FIG. 17 is a flow diagram of ending address processing of FIG. 15.

FIG. 16 is a flow diagram showing the operation of the beginning address processing process occurring in step 278 of FIG. 15. In step 286, the Address register 194 (shown in FIG. 9) is read to obtain the beginning pixel address. If the End of Integral marker is not present, the system has detected the start of a defect within the integral and stored this starting address, so that beginning address processing is exited from step 288. Otherwise, the beginning address processing continues with the Update Count being incremented in step 290. Next, in step 292, a provision, which will be explained in detail in reference to FIG. 17, is made for handling the condition in which a defect extends from one pixel to another. Then, the Defect Image History is updated in step 294, in a manner which will be explained in detail in reference to FIG. 19.

As previously described in reference to FIG. 10, to obtain valid results, it is necessary to center the static scan CCD sensor 7 on the second image resulting from each defect. This is achieved by listing only the address of the second image with various data collected during the linear scanning process. Thus, within beginning address processing, a check is made in step 296 to determine whether the current image is the second image of a defect. With the typical integration length of 30 microns, the second image is two integrals (or video scans) behind a similar first image. If the current image is determined to be the second image, the defect location is recorded with associated data in step 298. Whether the image is the first or second image, the data indicating the position (radius and angle) being inspected is updated, along with the autofocus data and prism position data, in step 300. If the new autofocus position differs from its previously logged position by a pre-determined threshold limit, as determined in step 302, autofocus mapping, along with positional and phase angle data occurs in step 304. Next, beginning address processing is exited.

FIG. 17 is a flow diagram showing the operation of the ending address processing occurring in step 284 of FIG. 15. The address register 194 is read in step 306, and a check for error conditions is made in step 308. Specifically, if the ending address is determined to be equal to zero or less than the current beginning address, a hardware error has occurred in VPB 164, so processing is terminated. Next, in step 310, a check is made to determine if the pixel width is less than a pre-set minimum, If it is, the processing of this particular ending address is exited. Next, in step 312, it is determined whether the adjacent defect image and the current image will fit within the bounding box used for static scanning with CCD sensor 7. If they will not fit, this ending address processing is exited after the pixel width of the previous image is enlarged in step 314. Otherwise, in step 316, the image data is recorded, including pixel addresses, the position (radius and angle) the autofocus and prism location settings, and the integral count. Then, in step 318, a determination is made of whether another image is already active within this integral. If it is not, an active image pointer is assigned to the current image in step 320. In either case, ending address processing is exited.

Figure 18:
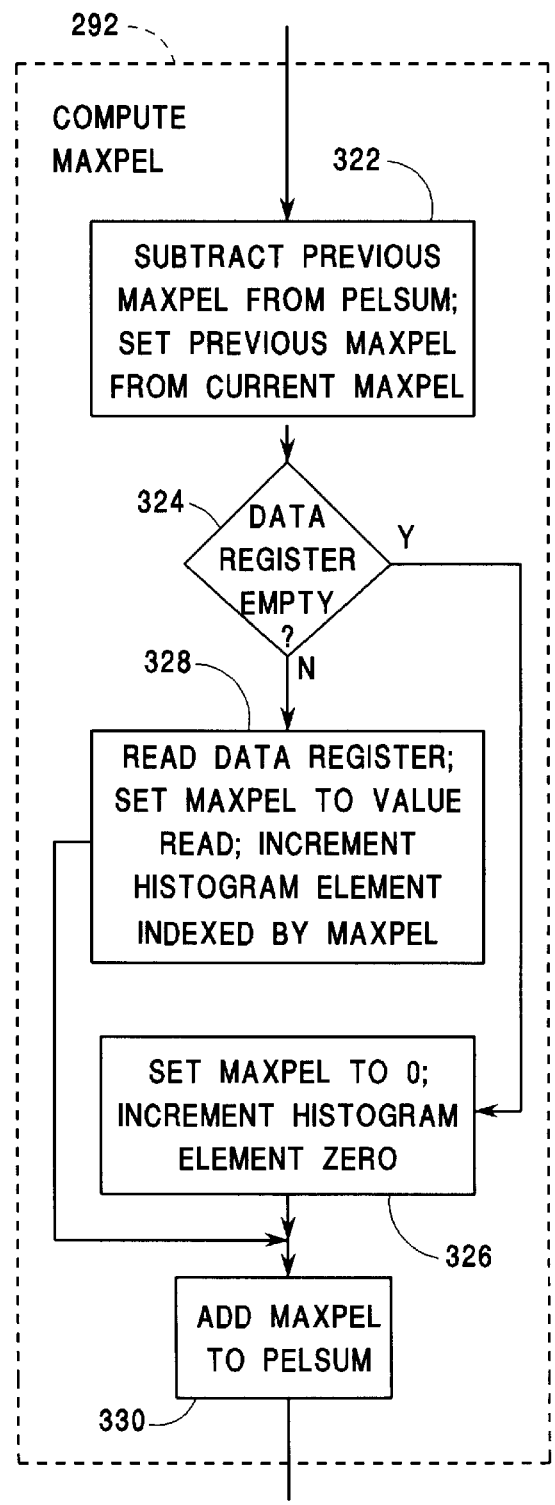
FIG. 18 is a flow diagram of a process for handling a large defect of FIG. 16.

FIG. 18 is a flow diagram showing the process of step 292 in FIG. 16, which is implemented to handle the condition in which a defect extends between sequentially adjacent integrals. In the absence of this type of provision, this condition presents the possibility of having a defect, which should be detected, but which is nevertheless not detected because, it contributes a portion of its resulting intensity to two integrals without raising the intensity of either of them to a level which is detected. To prevent this problem, a summed intensity, called PelSum is calculated for each sequentially adjacent pair of integrals, being determined for stored data in the form of the previous PelSum value, and from the current maximum intensity level, current MaxPel. In order to determine a new value for PelSum, in step 322, the previous value of MaxPel is subtracted from PelSum, and the Previous MaxPel is set to the level of the current MaxPel.

One of the forms of data being developed during this process is a histogram having elements corresponding to the various detected intensity values of MaxPel. Each time a value of MaxPel is determined, the histogram element indexed by the MaxPel value is incremented. In step 324, data register 195 is examined to determine if it is empty. It should not be empty, but if it is, in step 326, MaxPel is set to zero, and the histogram element 0 is incremented, indicating that a problem has occurred. If data is available from data register 195, in step 328, this value is read, and the histogram element indexed by this value is incremented. Finally, the new value for MaxPel is added to PelSum in step 330.

Figure 19:
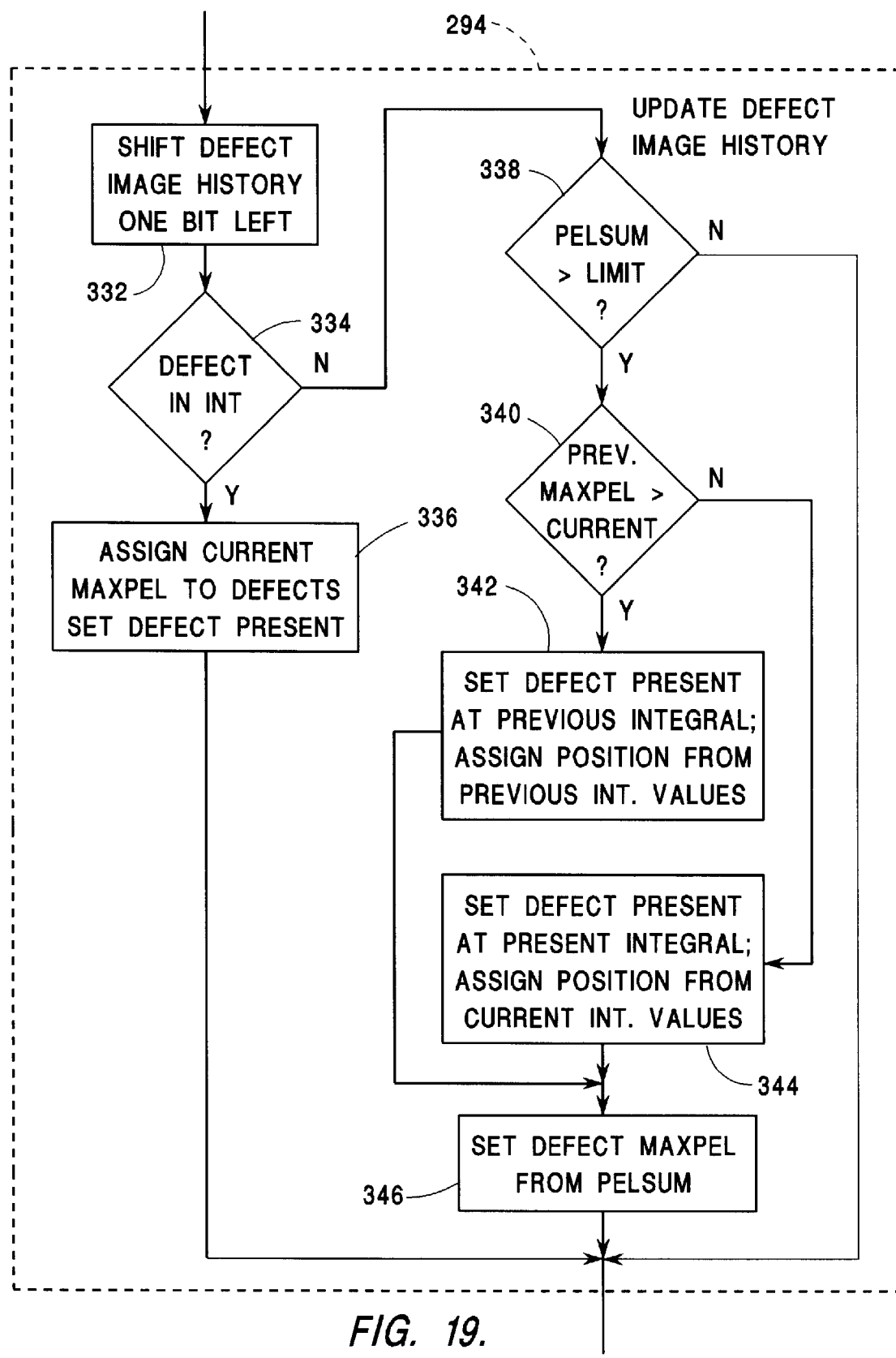
FIG. 19 is a flow diagram of a process for updating a Defect Image History Table of FIG. 16.

FIG. 19 is a flow diagram showing the process of step 294 in FIG. 16, in which the Defect Image History table is updated. First, in step 332, this table is shifted one bit to the left. Then, in step 334, it is determined if another active image is already in the current integral. If it is, in step 336, the current MaxPel is assigned to active defects in the integral, a defect present bit is set in the image history, and the current Defect MaxPel is set to the current MaxPel, and this step 294 is exited. On the other hand, if an active image is not already in the integral, as determined by step 334, a determination is made in step 338 of whether PelSum is above the beginning threshold 183 (shown in FIG. 8). If PelSum is not above this threshold, a defect is not considered detected, and this step 294 is exited. If PelSum is above this threshold level, a new defect is set, either in the current integral or in the previous integral, depending on which has the greater MaxPel value, thus a determination is made in step 340 of whether the previous MaxPel is greater than the present MaxPel. If the previous MaxPel is greater, in step 342, the Defect Present Bit is set in the Image History at the position corresponding to the previous integral, and defect position (radius and angle) values, an autofocus value, and a prism position value are assigned from the levels associated with the previous integral. If the current MaxPel is greater, in step 344, the Defect Present Bit is set at the position corresponding to the present integral, and these values are assigned the levels of the current integral. In either case, the Defect MaxPel is set from the PelSum in step 346, and the updating process of step 294 is exited.

Figure 20:
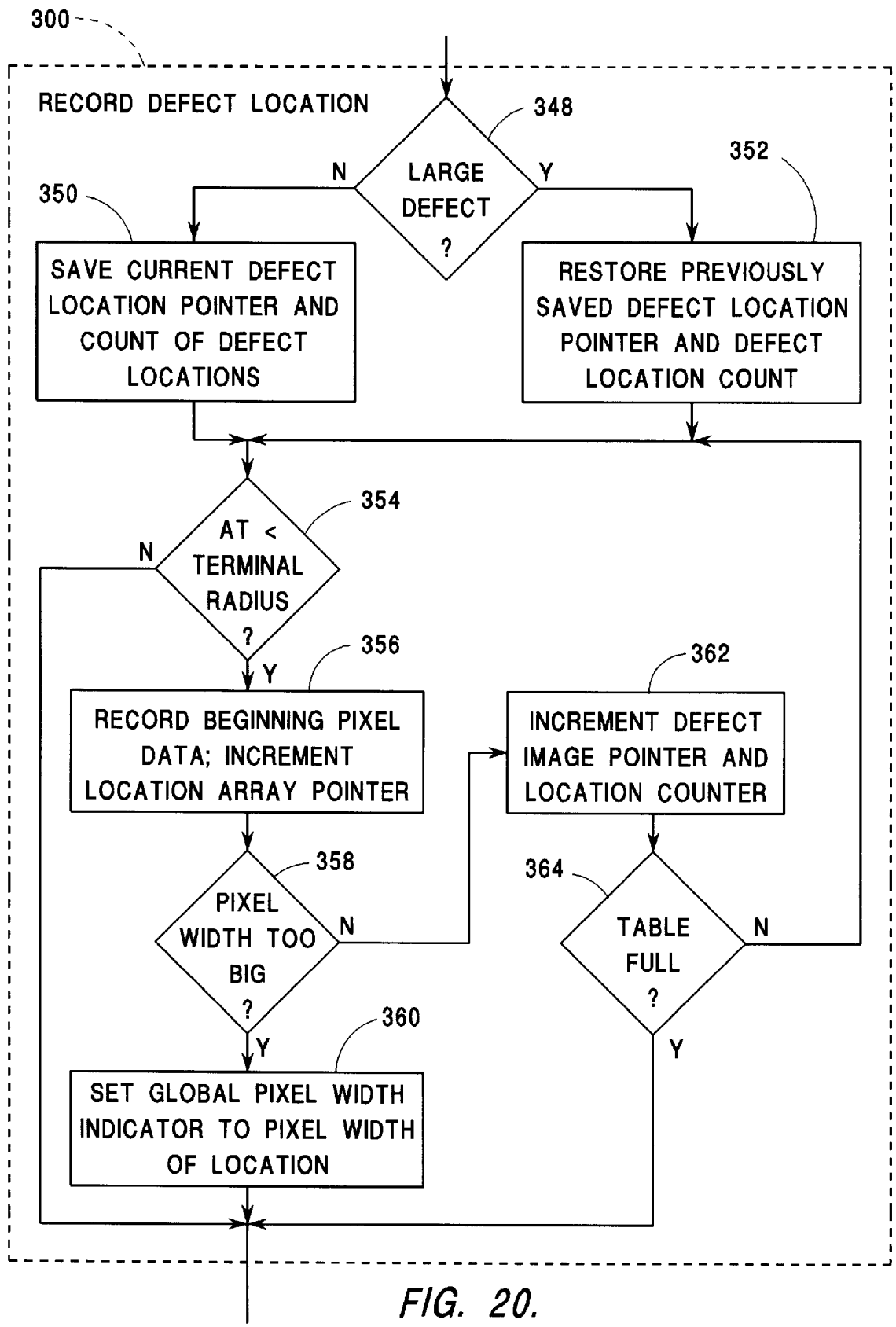
FIG. 20 is a flow diagram of a process for recording a defect location of FIG. 16.

FIG. 20 is a flow diagram showing the process of step 300 in FIG. 16, in which the defect location is recorded. First, a determination is made in step 348 of whether the defect being detected is a portion of a larger defect which has already been detected. If it is not part of a larger defect, as determined by looking at the results for the previous integral, the current Defect Location Pointer and the present Count of Defect Locations is saved in step 350. If it is part of a large defect, the previously saved Defect Location Pointer and the previous Defect Location Count are saved in step 352. In this way, only the defect image of the last integral is recorded for defects which span adjacent integrals.

Referring again to FIG. 10, the need for this procedure is illustrated by considering the interferogram pattern caused by a large defect. When such a pattern is viewed in the static scan process by array CCD sensor 7, if the large defect is located to extend downward from the center of bounding box 230, all of the image of the large defect within the bounding box consists of a valid positive image. If the bounding box is instead moved downward along the interferogram of the large defect, both positive and negative images will be present within the bounding box, producing invalid or indeterminant results.

Referring again to FIG. 20, if there is a defect image to record, and if the radial location of the defect is less that the terminal radius indicating the defect is within the active region being examined, as determined in step 354, defect data is recorded in step 356. Specifically, the beginning pixel address and width are recorded, along with the Defect MaxPel, location data, antofocus and prism location data, and the integral counter. The location of the Defect Location Array Pointer is also incremented. Next, a determination is made in step 358 of whether the defect is too wide, exceeding a maximum pixel width threshold. If it is too wide, in step 360, the global pixel width indicator is set to the pixel width of the location. If it is not too wide, in step 362, the Defect Image Pointer and Location Counter are incremented. Then if the Defect Location Table is full, as determined in step 364, the process of recording defect locations is exited. If this table is not full, the next defect in this integral, if there is one, as determined in step 345, is examined for recording.

Figure 21:
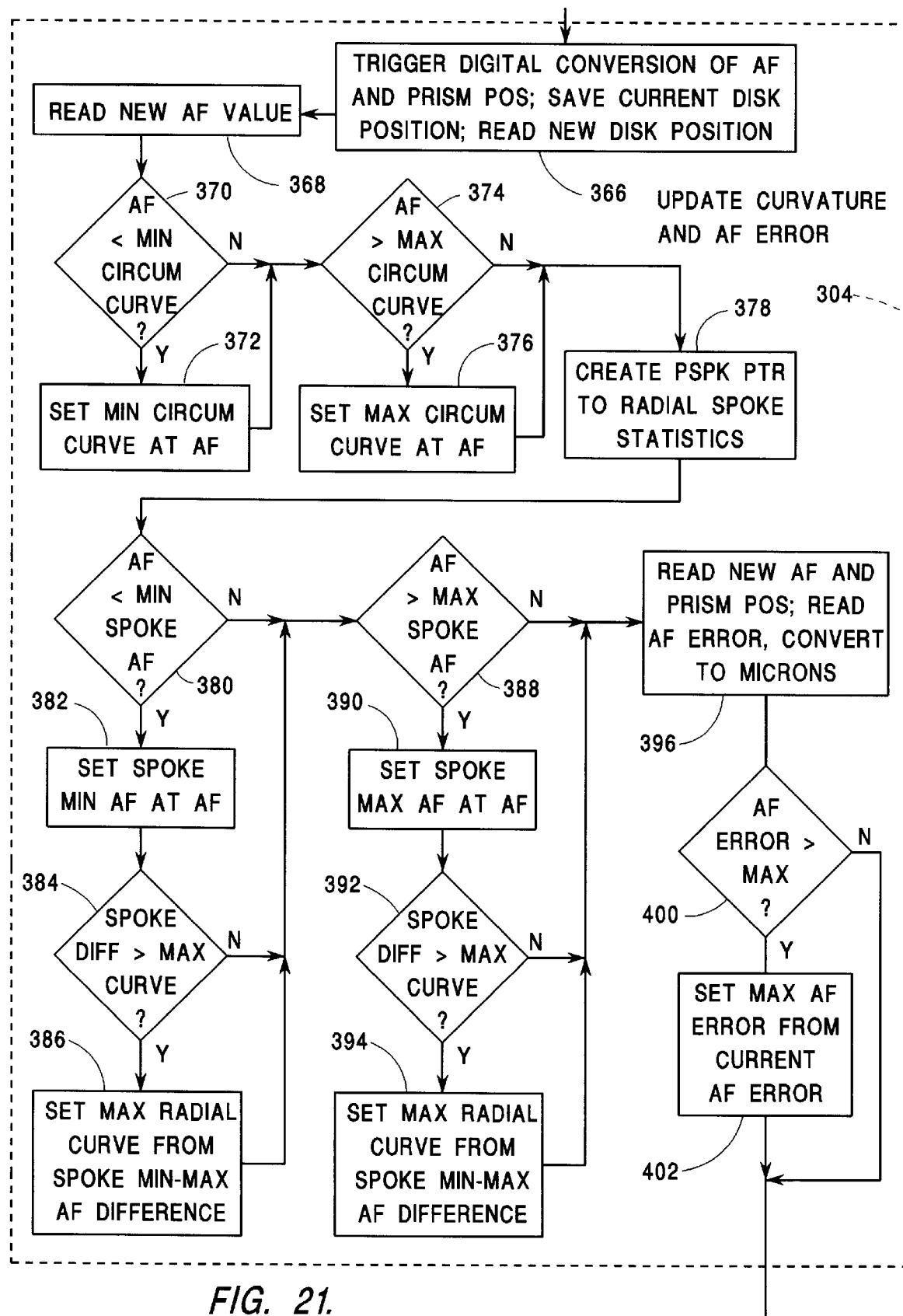
FIG. 21 is a flow diagram of a record autofocus mapping step of FIG. 16.

FIG. 21 is a flow diagram showing the operation of the record autofocus mapping step 304 in FIG. 16. In autofocus mapping, the current autofocus value is used to set circumferential and radial curvature characteristics describing certain features of the disk being tested. First, in step 366, the analog to digital conversion of autofocus and prism position signals is triggered, current position variables (radius and angle) are stored as previous, and new current position variables are read. Next, in step 368, a new autofocus value is read. This autofocus value is used to set or reset maximum and minimum values of a circumferential curvature variable indicating the flatness of the disk 2c being tested. If it is determined in step 370 that the autofocus value is less than the minimum circumferential curvature, the minimum circumferential curvature is set to the current autofocus value in step 372. If it is determined in step 374 that the autofocus level is greater than the maximum circumferential curvature, the maximum circumferential curvature is set to the autofocus value in step 376.

Next, in step 378, a spoke pointer, pSpk is created to allow the development of spoke statistics along a spoke, which is defined as a line extending outward from the center of the disk at the current angle. If it is determined in step 380 that the current autofocus value is less than the minimum autofocus for the spoke, in step 382 the spoke's minimum autofocus value is set from the current autofocus value. If it is determined in step 384 that the minimum to maximum autofocus difference is greater than the maximum radial curvature for the disk, in step 386 the maximum radial curvature is set from the minimum to maximum autofocus difference. If it is determined in step 388 that the current autofocus value is greater than the maximum autofocus value for the spoke, this latter value is set at the current autofocus value in step 390. If it is determined in step 392 that the minimum to maximum autofocus distance is greater than the maximum radial curvature for the disk, the maximum radial curvature is set from the minimum to maximum autofocus distance of the spoke in step 394. Next, in step 396, current values are read for the autofocus (lens position) and for the prism position. The codes for these variables are formed into a pair for storage.

A differential error signal indicating the focusing error, experienced in the subsystem for automatically focussing the lens 6, is generated from the difference between the outputs of photodetectors within the focus detector 8c. Since this error signal represents the ability of the autofocus signal to keep up with changes in the height of the disk 2c as it is rotated for inspection, and thereby to keep the interferometer 2 functioning properly, this error signal is also read in step 396, to be converted into an equivalent autofocus error in microns. Next, in step 400, the current autofocus error is compared with the currently stored maximum autofocus error. If the current autofocus error is greater, the maximum autofocus error is set to the new maximum level in step 402. In either case, the step 304 is next exited.

Figure 22:
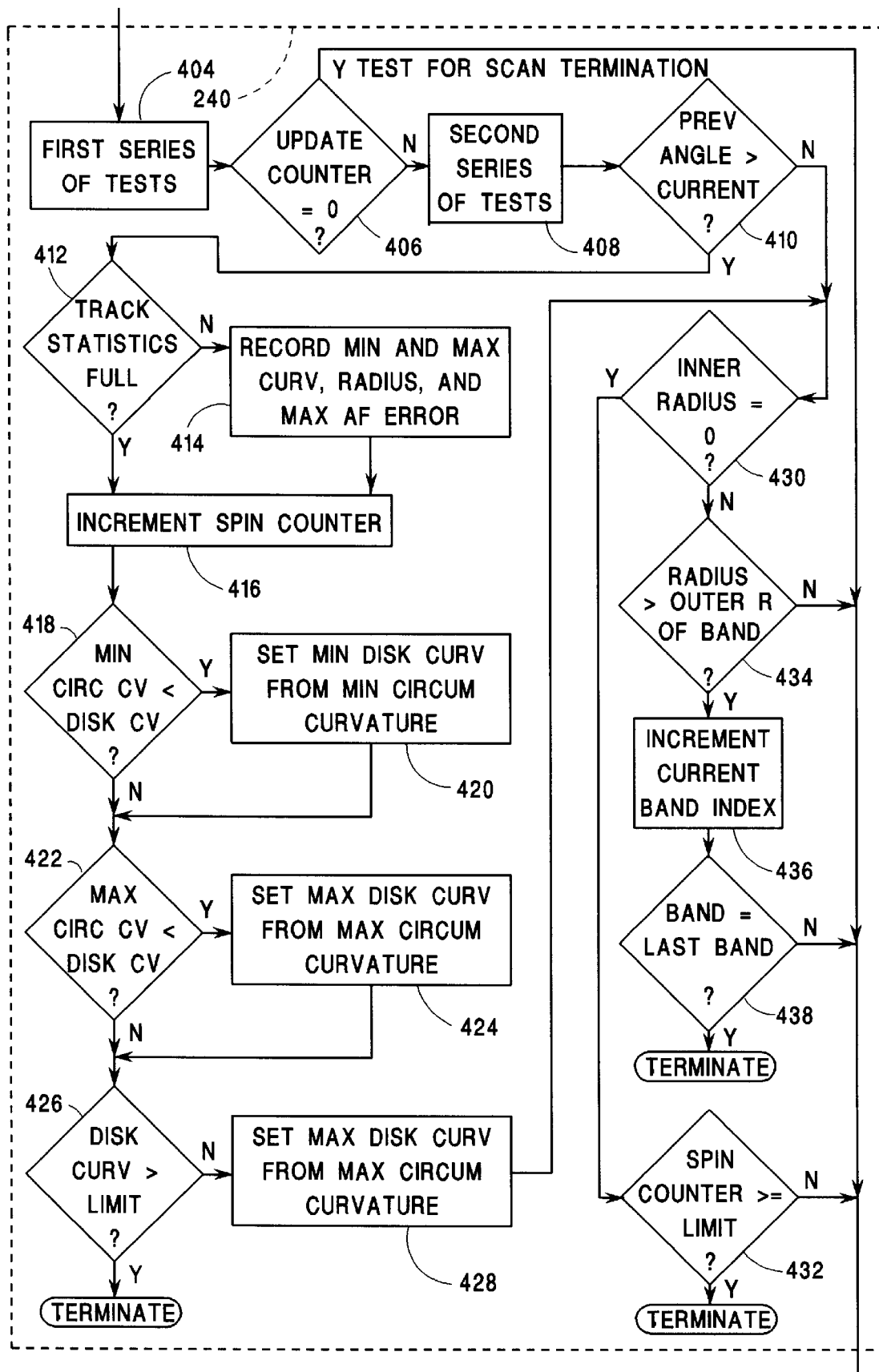
FIG. 22 is a flow diagram of a test for scan termination of FIG. 12.

FIG. 22 is a flow diagram showing the processes occurring in the test for scan termination of step 240 in FIG. 12. In a first series of tests occurring in step 404, a terminate condition is determined if the defect image table is full, if the defect location table is full, if the autofocus map table is full, if the pixel width exceeded a limit, if the scan time exceeded a time-out limit, if the address buffer 194 is full and latched, or if the data buffer 195 is full and latched. If any of these terminate conditions is met, the inspection process is terminated. The effect of termination is shown in FIG. 12. Next, in step 406, the Update Counter is tested to see if it equals zero. If it equals zero at this point, it has been set to zero at the start of the defect scan, so the scan termination testing is exited. In a second series of tests occurring in step 408, a number of other termination conditions are checked. The process is terminated if the current angle is greater than the maximum (360 degree) angle, indicating that the turntable encoder 198 (shown in FIG. 6) counted too many bits, if the Defect Image Count exceeds the Limit in Band (which is a pre-determined maximum number of defects allowable in an annular portion of the disk 2c), if the circumferential curvature exceeds the Limit in Band (which is a pre-determined maximum allowable curvature within an annular portion of the disk), or if the maximum radial curvature exceeds the Limit in Band.

Next, in step 410, a determination is made of whether the previous angle is greater than the current angle. If it is, a full revolution has been completed by the turntable 2e (shown in FIG. 1), passing the 0-degree angle indicating the start of a new revolution. If this has occurred, a number of operations occurring at the end of a full revolution are performed. First, a test is performed in step 412 to determine if the Track Statistic Array is full. If it is not full, various statistics for the track—minimum and maximum curvature, radius, and maximum autofocus error—are recorded in step 414. In either case, the spin counter is incremented in step 416, and a test is made in step 418 to determine if the minimum circumferential curvature is set at a value less than the disk curvature. If it is, in step 420, the minimum disk curvature is set at the level of the minimum circumferential curvature. Similarly, a test is them made in step 422 to determine if the maximum circumferential curvature is set at a value less than the disk curvature. If it is, the maximum disk curvature is set to the level of the maximum circumferential curvature in step 424. Next, in block 426, a determination is made of whether the disk curvature exceeds the Limit in Band. If it does, the process is terminated; otherwise, in step 428, the maximum disk curvature is set from the maximum circumferential curvature.

On the other hand, if it is determined in step 410 that a complete revolution has not been completed, the various processes described above as following step 410 are not required. In either case, in step 430, a determination is made of whether the inner radius is zero. If it is, it is known that the inner radius has been set to zero to perform a special diagnostic procedure in which the turntable 2e is rotated without moving the interferometer 2 (both shown in FIG. 1). In such a test, the number of rotations desired is initially set as a limit; so if the inner radius is zero, in step 432, the spin counter is checked against this limit. If the limit has been reached, the process is terminated, as it has been completed; otherwise the test for termination step 240 is exited.

If it is determined in step 430 that the inner radius is not zero, a full-disk inspection is in progress. The concept of bands has been implemented to allow variations in inspection criteria for different bands, or annular areas, within the active area of the disk. Thus, in step 434, the radial position of carriage 159 is compared to the outer radius of the current band. If the current radius is not greater than the outer radius of the band, the test for termination step 240 is exited. If the current radius is greater than the outer radius of the current band, the current band index is incremented in step 436. If the new current band is equal to the max band limit, as determined in step 438, the test is terminated, as it has been completed; otherwise the test for termination is exited.

As previously mentioned in reference to FIG. 11, the process of generating profiles of individual defects with the narrow-scanning interferometer 2a may be started as soon as there are sufficient defects in the defect table to examine, or it may wait until the entire area of interest has been scanned by the wide-scanning interferometer 2.

Referring again to FIGS. 3–5, the generation of a defect profile will now be described. The relative illumination intensities measured at photodetectors 66, 68 provide an indication of relative intensities of the polarization along the major and minor axes of the elliptical polarization indicated by ellipse 60, and hence of the phase shift between the returning sub-beams 48, 50. This phase shift is a function of the relative heights of test spots 54, 56 and of parameters within the interferometer 2a. The elliptically polarized return beam exiting half-wave plate 30 may be mathematically broken into an X-vector, $V_x$, describing light polarized in the direction indicated by arrow 28, and a Y-vector, $V_y$, describing light polarized in the direction indicated by arrow 44. The values of these vectors are given as a function of the time variable, t, by:

$$V_x = A_0 \sin(\omega t + kL + 2kd + \phi_0) \tag{1}$$

$$V_y = A_0 \sin(\omega t + kL) \tag{2}$$

Thus, the X- and Y-vectors have the same amplitude, $A_0$, differing only in phase angle. In these equations, $\omega$ is the angular frequency of the laser beam, in radians per second, L is the original length of the light path, which does not matter because it has the same effect on both equations (1) and (2), d is the height difference which is being measured by this process, $\phi_0$ is an original phase angle, which is the phase angle provided by the apparatus when the test spots 54, 56 are at the same height, and k is a wave number, which is defined as follows:

$$k = \frac{2\pi}{\lambda} \tag{3}$$

In this expression, λ is the wavelength of the laser beam. To simplify the following mathematical derivation, these equations are rewritten using complex notation as:

$$V_x = A_0 e^{i(\omega t + kL + 2kd + \phi_0)} \tag{4}$$

$$V_y = A_0 e^{i(\omega t + kL)} \tag{5}$$

After passing through the beamsplitter 25, the elliptically polarized return beam 62 is broken into sub-beams within polarizing beamsplitter 64. Since the beamsplitter 25, being a non-polarizing type, handles differing polarities in the same way, losses in the transmission through this beamsplitter 25 are not considered, as it is determined that the light level at photodetector 68 is given by:

$$V_s = V_x \cos 45° + V_y \cos 45° \tag{6}$$

$$V_s = \frac{\sqrt{2}}{2} A_0 [e^{i(\omega t + kL + 2kd + \phi_0)} + e^{i(\omega t + kL)}] \tag{7}$$

Similarly, the light level at photodetector 66 is given by:

$$V_p = \frac{\sqrt{2}}{2} A_0 [e^{i(\omega t + kL + 2kd + \phi_0)} - e^{i(\omega t + kL)}] \tag{8}$$

The light intensity measured at photodetector 68 is obtained by multiplying $V_s$ times its conjugate, resulting in the following equation:

$$I_1 = \frac{A_0^2}{2} [e^{i(\omega t + kL + 2kd + \phi_0)} + e^{i(\omega t + kL)}][e^{-i(\omega t + kL + 2kd + \phi_0)} + e^{-i(\omega t + kL)}] \tag{9}$$

Next, $I_0$ is defined as equal to the square of $A_0$, the imaginary portion of the above equation is eliminated, and the real portion of the equation is rewritten as:

$$I_1 = \frac{I_0}{2}[2 + \cos(2kd + \phi_0)] \tag{10}$$

$$I_1 = I_0\cos^2\left(kd + \frac{\phi_0}{2}\right) \tag{11}$$

Similarly the beam intensity at sensor 66 is given by:

$$I_2 = I_0\sin^2\left(kd + \frac{\phi_0}{2}\right) \tag{12}$$

The preceding discussion assumes that the incoming laser beam 14, which is directed downward at the half-wave plate 30, is perfectly polarized in the direction of arrow 28 when it enters the half-wave plate 30. In other words, the preceding discussion assumes the following equations to be true:

$$I_x = I_0 \tag{13};$$

$$I_y = 0 \tag{14}$$

A more realistic mathematical model is given by the following equations, in which $\Gamma$ has a value, depending on various aspects of the apparatus, between 0 and 1. If the input beam from the laser entering half-wave plate 30 is entirely polarized in the x-direction indicated by arrow 28, $\Gamma$ is equal to one. If this beam is entirely polarized in the y-direction indicated by arrow 44 (shown in FIG. 5), $\Gamma$ is equal to zero.

$$I_x = \Gamma I_0 \tag{15}$$

$$I_y = (1-\Gamma)I_0 \tag{16}$$

Under these conditions, the illumination intensity, $I_1$, of the beam impinging on photodetector 68, and the illumination intensity, $I_2$, of the beam impinging on photodetector 66. are given by the following equations:

$$I_1 = \Gamma I_0 \cos^2\left(kd + \frac{\phi_0}{2}\right) + (1-\Gamma)I_0\sin^2\left(kd + \frac{\phi_0}{2}\right) \tag{17}$$

$$I_2 = \Gamma I_0 \sin^2\left(kd + \frac{\phi_0}{2}\right) + (1-\Gamma)I_0\cos^2\left(kd + \frac{\phi_0}{2}\right) \tag{18}$$

The mathematics associated with these intensities is simplified by considering the sum and differences of Equations (17) and (18), yielding the following results:

$$I_1 - I_2 = (2\Gamma - 1)I_0 \cos(2kd + \phi_0) \tag{19}$$

$$I_1 + I_2 = I_0 \tag{20}$$

A differential intensity parameter is formed by dividing the difference between the illumination intensity signals by their sum. Thus, this differential intensity parameter S is given by the following equation:

$$S = \frac{I_1 - I_2}{I_1 + I_2} = (2\Gamma - 1)\cos(2kd + \phi_0) \tag{21}$$

The interferometer 10 can be adjusted, particularly by moving the Wollaston prism 34 in the directions indicated by arrow 28, so that $\phi_0$ is equal to 0, $\pi/2$, or another convenient value. Such an adjustment may, for example, be made so that, when a flat test surface 12 is imaged, the output values of the two photodetectors 66, 68 are equal.

Next $\phi_0$ is set to $-\pi/2$, so that S is expressed as:

$$S = (2\Gamma - 1)\sin 2kd = (2\Gamma - 1)\sin\left(\frac{4\pi d}{\lambda}\right) \tag{22}$$

With this substitution, S has the same sign as d. Equation (22) is in a form which can be solved for the distance d, yielding:

$$d = \left(\frac{\lambda}{4\pi}\right)\arcsin\left(\frac{S}{2\Gamma - 1}\right) \tag{23}$$

This equation holds true as long as the following relationships are met:

$$0 \leq \Gamma \leq 1 \tag{24};$$

$$\Gamma \neq 1/2 \tag{25}$$

Thus, during measurement processes, a program is executed in processor 78 to determine the difference in height between the two test spots 54, 56, indicated as d in the equations, by substituting the illumination intensity values, indicated in the equations as $I_1$ and $I_2$ in the equations, measured by photodetectors 66, 68, into the equations (22) and (23).

Figure 5A:
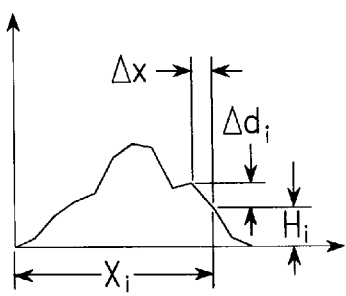
FIG. 5A is a graphical view of a method for determining the profile of a large defect using the interferometer of FIG. 3.

FIG. 5A is a graphical representation of the process of determining the profile of a relatively large anomaly in a test surface with operation of the apparatus in the preferred mode defined above. Each measurement made yields a calculated change in height, indicated as $\Delta d_j$, occurring across an incremental distance, indicated as $\Delta x$, which is equal to the distance between test spots 54, 56. For example, the scanning motion occurs at a constant speed, with the outputs of photodetectors 66, 68 being sampled periodically at times corresponding to scanning through the distance $\Delta x$. This distance may be, for example, 2 microns. The horizontal and vertical coordinates to a measured point i on the surface of the anomaly, indicated as $X_i$ and $H_i$, respectively, are calculated using the following equations:

$$X_i = i\Delta x \tag{26}$$

$$H_i = \sum_{j=0}^{i} \Delta d_j \tag{27}$$

Thus, the program executing in processor 72 also performs a profile development function by calculating horizontal distance and height information using the equations (26) and (27). While the term "height" is used to indicate a vertical distance above the nominally flat surface of the surface 12 under test, or an upward sloping portion of an anomaly, it is understood that negative values for "height" indicate a vertical distance below the nominally flat surface of the surface 12 under test or a downward sloping portion of an anomaly. The lateral resolution depends on the sub-beam spot sizes and on the separation distance between the two beams. The vertical resolution depends on the signal-to-noise ratio implicit in the calculation of the differential intensity parameter, S. This signal-to-noise ratio in turn depends on the stability of the system, on the laser intensity and level of fluctuation, on the contrast ration, and on the dark current, noise levels, and sensitivity of the photodetectors 66, 68. Using apparatus of this sort, a vertical resolution of 1 nanometer can be achieved.

If the defect or anomaly is quite large, this method may be used to produce a number of profiles representing sections of the anomaly at various radial distances from the center of the disk.

While the invention has been described in its preferred form or embodiment with some degree of particularity, it is understood that this description has been given only by way of example and that numerous changes in the details of construction, fabrication and use, including the combination and arrangement of parts, may be made without departing from the spirit and scope of the invention.

What is claimed is:

1. Inspection apparatus for inspecting a surface of a sample, wherein said apparatus comprises:

a wide scanning interferometer determining locations of surface defects;

a narrow scanning interferometer determining the profiles of said surface defects located by said wide scanning interferometer; and means for establishing relative motion between said sample and said wide scanning and narrow scanning interferometers, with said surface adjacent to said wide scanning and narrow scanning interferometers.

2. The inspection apparatus of claim 1, wherein said means for establishing relative motion includes:

first drive means for moving said sample in a first direction;

second drive means for moving said wide scanning interferometer in a second direction; and third drive means for moving said narrow scanning interferometer in a third direction.

3. Inspection apparatus for inspecting a surface of a sample, wherein said apparatus comprise:

a wide scanning interferometer determining locations of surface defects;

a narrow scanning interferometer determining the profiles of said surface defects located by said wide scanning interferometer; and means for establishing relative motion between said sample and said wide scanning and narrow scanning interferometers, with said surface adjacent to said wide scanning and narrow scanning interferometers, wherein said means for establishing relative motion includes first drive means for rotating said sample about an axis, second drive means for moving said wide scanning interferometer in a first direction extending radially away from said axis, and third drive means for moving said narrow scanning interferometer in a second direction extending radially away from said axis.

4. The inspection apparatus of claim 1, wherein said wide-scanning interferometer forms an interferogram along a linear CCD array, wherein a difference in illumination within said interferogram is brought about by a corresponding defect on said surface of said sample.

5. The inspection apparatus of claim 5, wherein said interferogram is bright in areas corresponding to defects on said surface of said sample and dark in areas corresponding to flat portions of said surface of said sample.

6. Inspection apparatus for inspecting a surface of a sample, wherein said apparatus comprises:

a wide scanning interferometer determining locations of surface defects, wherein said wide-scanning interferometer is a common mode shearing type including a first laser light source, a first beamsplitter directing an illumination beam from said first laser light source in a first direction, a first Wollaston prism assembly breaking said illumination beam into a pair of sheared illumination sub-beams separated in a second direction, a first objective lens, through which through which said illumination sub-beams are directed to reflect from said surface of said sample, and through which return sub-beams reflected from said surface of said sample are transmitted back to said first Wollaston prism assembly, and a line scan sensor into which a return beam is projected from said first Wollaston prism assembly in a direction opposite said first direction, with an interferogram of said surface of said sample being formed on said line scan sensor, and with said line scan sensor providing, as an output, a first signal responsive to variations in said interferogram;

a narrow scanning interferometer determining the profiles of said surface defects located by said wide scanning interferometer; and means for establishing relative motion between said sample and said wide scanning and narrow scanning interferometers, with said surface adjacent to said wide scanning and narrow scanning interferometers.

7. The inspection apparatus of claim 6, wherein said first Wollaston prism assembly within said wide-scanning interferometer has:

a first half-wave plate through which said illumination beam is directed into said first Wollaston prism assembly;

a first Wollaston prism adjacent said first half wave plate;

a second half-wave plate adjacent said first Wollaston prism on a side thereof opposite said first half-wave plate; and a second Wollaston prism adjacent said second half-wave plate.

8. The inspection apparatus of claim 6, wherein said line scan sensor in said wide-scanning interferometer is a linear array of charge coupled devices.

9. The inspection apparatus of claim 6, wherein said wide-scanning interferometer includes:

an actuator driving said first Wollaston prism assembly in said second direction; and a phase detector determining a phase shift between said return sub-beams, with an output of said phase detector driving said actuator to maintain darkfield conditions in said interferogram, except for illumination areas within said interferogram corresponding to defects in said surface of said sample.

10. The inspection apparatus of claim 6, wherein said narrow-scanning interferometer includes:

a second laser light source producing a coherent, linearly polarized beam;

optical apparatus, wherein said coherent, linearly polarized beam is decomposed into first and second projected sub-beams, with said first projected sub-beam being linearly polarized in a third direction, with said second projected sub-beam being linearly polarized in a fourth direction, perpendicular to said first direction, wherein said first projected sub-beam is projected to a first test spot on said surface of said sample, wherein said second projected sub-beam is projected to a second test spot on said surface of said sample, in a spaced-apart relationship with said first test spot, and wherein said first and second projected sub-beams, after reflection from said first and second test spots, are recombined into a single, elliptically polarized returning beam;

a polarizing beamsplitter in which said elliptically polarized returning beam is split into a first returning sub-beam polarized in a fifth direction and a second returning sub-beam, polarized in a sixth direction, parallel to said fifth direction;

a first photodetector measuring intensity of said first returning sub-beam; and a second photodetector measuring intensity of said second returning sub-beam.

11. The inspection apparatus of claim 10, wherein said optical apparatus includes:

a third Wollaston prism, wherein said coherent, linearly polarized beam is decomposed into said first and second projected sub-beams, and wherein said first and second projected sub-beams, after reflection from said first and second test spots, are recombined into said single, elliptically polarized returning beam; and a second objective lens, disposed between said Wollaston prism and said surface of said sample, wherein said first objective lens focusses said first projected sub-beam on said first test spot and said second projected sub-beam on said second test spot.

12. The inspection apparatus of claim 10, comprising additionally:

defect detection means for detecting variations in said first signal;

data storage means;

first location sensing means providing first location data describing movement of said surface of said sample past said wide-scanning interferometer;

second location sensing means providing second location data describing movement of said surface of said sample past said narrow-scanning interferometer;

first control means storing said first location data within said data storage means in response to said defect detection means; and second control means operating said means for establishing relative motion to move portions of said surface corresponding to said first location data stored in said data storage means past said narrow-scanning interferometer.

13. The inspection apparatus of claim 12:

wherein said means for establishing relative motion includes first drive means for rotating said sample about an axis, second drive means for moving said wide-scanning interferometer in a first radial direction extending radially away from said axis, and third drive means for moving said narrow-scanning interferometer in a second radial direction extending radially away from said axis;

wherein said first location data represents positions of said first and second drive means;

wherein said second location data represents positions of said first and third drive means;

wherein said first location data is generated as said sample is rotated by said first drive means with movement of said second drive means; and wherein said second control means operates said third drive means as said sample is rotated by said first drive means.

14. The inspection apparatus of claim 13:

wherein said line scan sensor of said wide-scanning interferometer includes a plurality of photosensitive elements extending in a line perpendicular to a direction of motion of said interferogram caused by movement of said test surface adjacent said wide-scanning interferometer; and wherein outputs of said photosensitive elements are sampled on a periodic basis, with an output of each said photosensitive element being responsive to an integrated sum of illumination received between sampling.

15. The inspection apparatus of claim 14:

wherein said wide-scanning interferometer produces first and second lines of illumination on said surface of said sample, said first and second lines of illumination being separated in a direction along a path of said relative motion between said wide-scanning interferometer and said sample by a shearing distance; and wherein said test specimen is driven at a speed so that said surface of said sample moves along said path of said relative motion through an integral distance, which is a submultiple of said shearing distance, between times at which said photosensitive elements are sampled.

16. The apparatus of claim 15:

wherein said first control means includes means responsive to sequential operation of said defect detection means as a surface defect of said test surface moves past said first and second lines of illumination; and wherein said first control means stores said location data within said data storage means in response to operation of said defect detection means as said surface defect moves past said second line of illumination.

17. The apparatus of claim 16:

wherein said first control means includes means responsive to continued operation of said defect detection means as a large surface defect of said test surface, said large surface defect being longer in a direction along said preferred path of motion than said integral distance, moves by said first objective lens; and wherein said first control means stores said first location data within said data storage means in response to a last operation of said defect detection means as said large surface defect moves by said first objective lens.

18. The apparatus of claim 14:

wherein said defect detection means provides an intensity level signal indicating an integrated illumination level received between sampling; and wherein said first control means stores said location data within said data storage means in response to operation of said defect detection means at sequential samples of said photosensitive elements.

19. A method for inspecting a surface of a sample, wherein said method comprises:

placing said sample on a turntable for rotation about an axis of rotation of said turntable with said surface of said sample being outwardly exposed from said turntable;

moving a wide-scanning optical inspection device adjacent said surface of said sample in a first direction radial to said axis of rotation, with said wide-scanning optical device detecting defects within said surface as said sample is rotated by said turntable, and with a location of each defect detected by said wide-scanning optical device being stored in data storage means;

moving a narrow-scanning optical inspection device adjacent said surface of said sample in a second direction radial to said axis of rotation among radial distances corresponding to each said location of each said defect previously detected by said wide-scanning optical device, with said narrow-scanning optical device providing signals representative of a surface profile of each said defect previously detected by said wide-scanning optical device as said sample is rotated by said turntable; and calculating said surface profile of each said defect within computing means from said signals representative of said surface profile.

20. The method of claim 19, wherein said surface of said sample is entirely traversed by said wide-scanning optical inspection device before said narrow-scanning device is moved among radial distances corresponding to each said location of each said defect previously detected by said wide-scanning optical device.

21. The method of claim 19, wherein said narrow-scanning device is moved among radial distances corresponding to locations of said defects previously detected by said wide-scanning optical device before said surface of said sample is entirely traversed by said wide-scanning optical inspection device.

22. The method of claim 19, wherein said wide-scanning optical device is a common mode shearing, wide-scanning interferometer including:

a first laser light source;

a first beamsplitter directing an illumination beam from said first laser light source in a first direction;

a first Wollaston prism assembly breaking said illumination beam into a pair of sheared illumination sub-beams separated in a second direction;

a first objective lens, through which through which said illumination sub-beams are directed to reflect from said surface of said sample, and through which return sub-beams reflected from said surface of said sample are transmitted back to said first Wollaston prism assembly; and a line scan sensor into which a return beam is projected from said first Wollaston prism assembly in a direction opposite said first direction, with an interferogram of said surface of said sample being formed on said line scan sensor, and with said line scan sensor providing, as an output, a first signal responsive to variations in said interferogram.

23. The method of claim 19:

wherein said line scan sensor of said wide-scanning interferometer includes a plurality of photosensitive elements extending in a line perpendicular to a direction of motion of said interferogram caused by movement of said test surface adjacent said wide-scanning interferometer; and wherein outputs of said photosensitive elements are sampled on a periodic basis, with an output of each said photosensitive element being responsive to an integrated sum of illumination received between sampling.

24. The method of claim 19, wherein said narrow-scanning optical device is a narrow-scanning interferometer including:

a second laser light source producing a coherent, linearly polarized beam;

optical apparatus, wherein said coherent, linearly polarized beam is decomposed into first and second projected sub-beams, with said first projected sub-beam being linearly polarized in a third direction, with said second projected sub-beam being linearly polarized in a fourth direction, perpendicular to said first direction, wherein said first projected sub-beam is projected to a first test spot on said surface of said sample, wherein said second projected sub-beam is projected to a second test spot on said surface of said sample, in a spaced-apart relationship with said first test spot, and wherein said first and second projected sub-beams, after reflection from said first and second test spots, are recombined into a single, elliptically polarized returning beam;

a polarizing beamsplitter in which said elliptically polarized returning beam is split into a first returning sub-beam polarized in a fifth direction and a second returning sub-beam, polarized in a sixth direction, parallel to said fifth direction;

a first photodetector measuring intensity of said first returning sub-beam; and a second photodetector measuring intensity of said second returning sub-beam, with said signals representative of a surface profile including output signals of said first and second photodetectors.

* * * * *